(12) United States Patent
Coleman et al.

(10) Patent No.: US 8,460,862 B2
(45) Date of Patent: Jun. 11, 2013

(54) ENZYME SUBSTRATES FOR VISUALIZING ACIDIC ORGANELLES

(75) Inventors: Daniel J. Coleman, Corvallis, OR (US); John J. Naleway, Eugene, OR (US)

(73) Assignee: Marker Gene Technologies, Eugene, OR (US)

( * ) Notice: Subject to any disclaimer, the term of this patent is extended or adjusted under 35 U.S.C. 154(b) by 319 days.

(21) Appl. No.: 12/381,560

(22) Filed: Mar. 11, 2009

(65) Prior Publication Data

US 2010/0233744 A1  Sep. 16, 2010

(51) Int. Cl.
*C12Q 1/00* (2006.01)

(52) U.S. Cl.
USPC ........ 435/4; 435/18; 435/20; 435/21; 435/22; 435/23; 435/24

(58) Field of Classification Search
USPC .......................... 435/4, 18, 20, 21, 22, 23, 24
See application file for complete search history.

(56) References Cited

U.S. PATENT DOCUMENTS

| 5,089,392 | A * | 2/1992 | Miller et al. | 435/21 |
| 5,869,689 | A * | 2/1999 | Zhang et al. | 548/405 |
| 2008/0248041 | A1 * | 10/2008 | Fujii et al. | 424/139.1 |
| 2010/0062460 | A1 * | 3/2010 | Pande et al. | 435/7.2 |
| 2010/0093004 | A1 * | 4/2010 | Patton et al. | 435/7.24 |

OTHER PUBLICATIONS

Ron et al. Blood Cells, Molecules and Diseases (2005) 35: 57-65.*
Streitweiser et al. "Introduction to Organic Chemistry" 1981. second edition. (Macmillan Publishing Co., Inc.: New York) p. 735.*
Miller et al. J. Org. Chem. (1991) 56: 30-34.*

* cited by examiner

*Primary Examiner* — Susan Hanley
(74) *Attorney, Agent, or Firm* — Timothy McCutcheon

(57) ABSTRACT

The present invention relates to the visualization of acidic organelles based upon organelle enzyme activity. The organelle substrates of the invention are specific for enzyme activity of the organelle and label these organelles, such as lysosomes, rendering them visible and easily observed. Substrates of the present invention include substrates that produce a fluorescent signal. The fluorogenic acidic organelle enzyme substrates of this invention are designed to provide high fluorescence at low pH values and are derivatized to permit membrane permeation through both outer and organelle membranes of intact cells and can be used for staining cells at very low concentrations. They can be used for monitoring enzyme activity in cells at very low concentrations and are not toxic to living cells or tissues.

20 Claims, 11 Drawing Sheets

Figure 1. Fluorescein Based Staining Probes (Green Fluorescence).
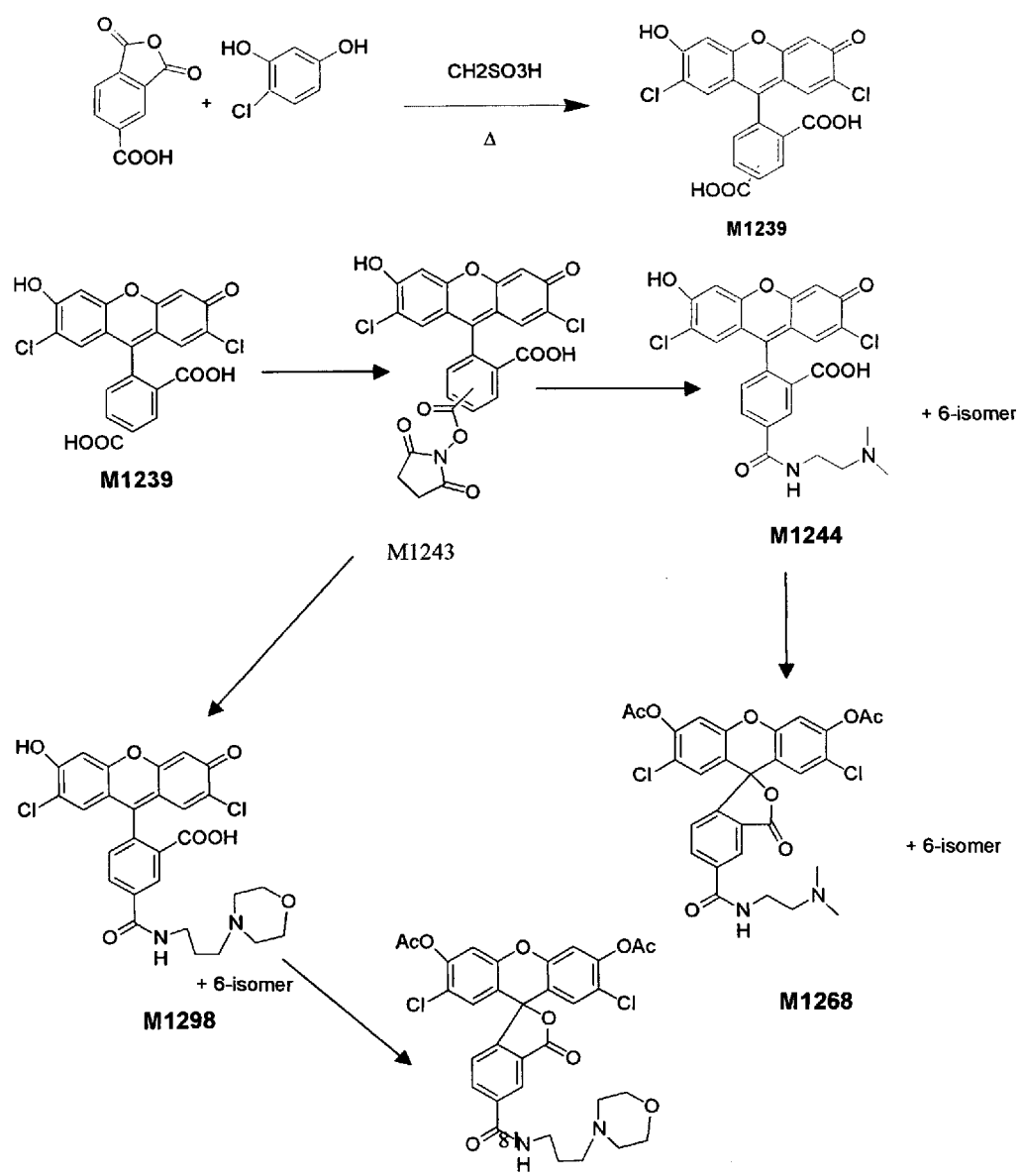

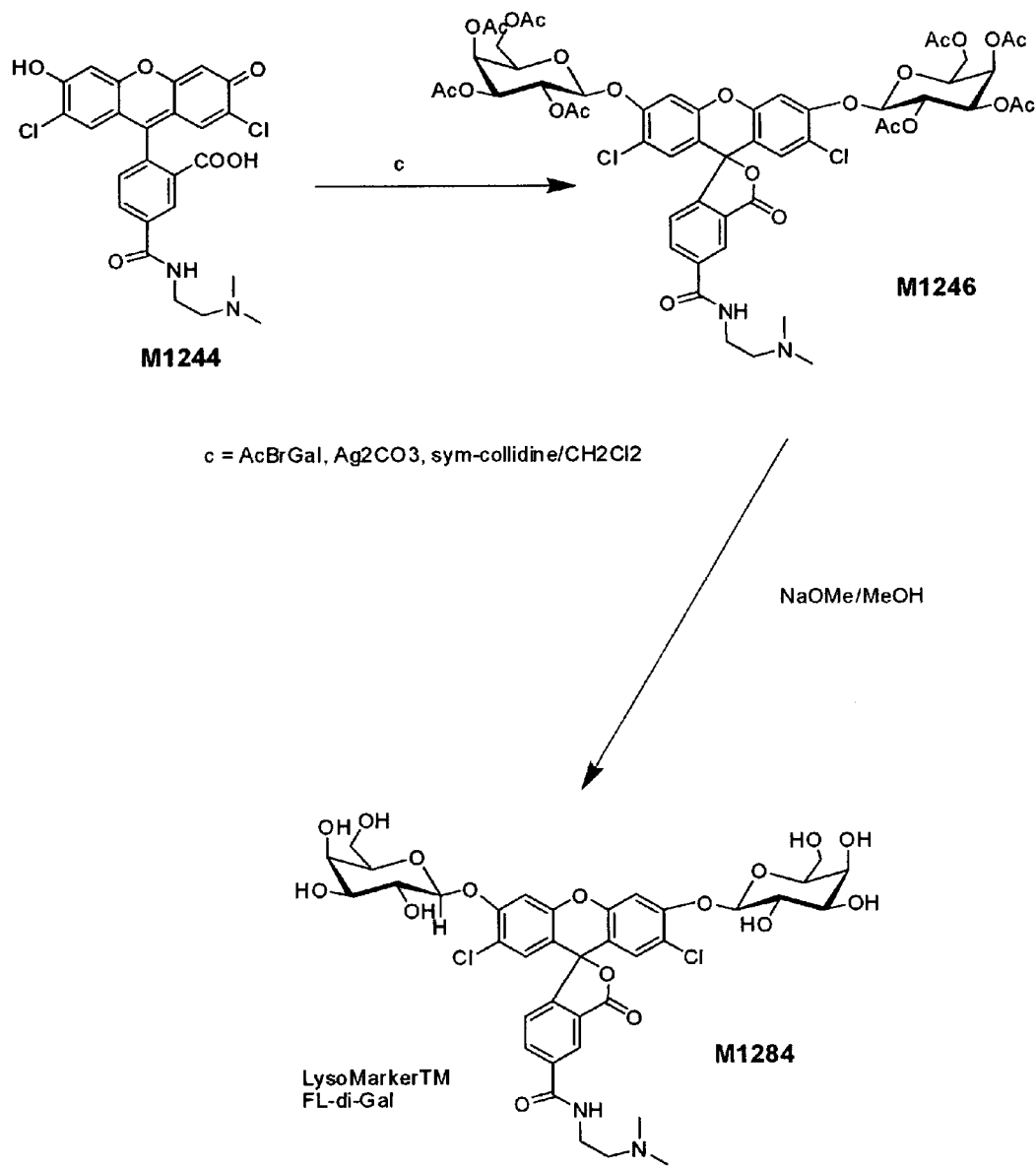
Figure 2. Krabbe LysoMarker™ Substrates.

Figure 2. (continued) Krabbe LysoMarker™ Substrates.
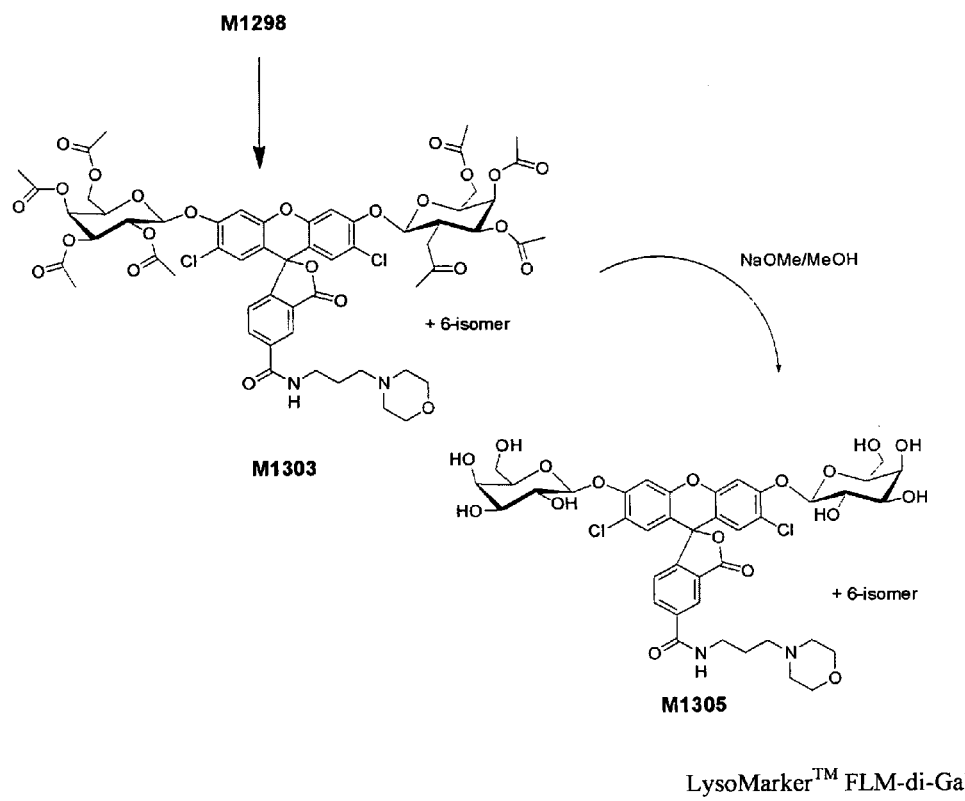
LysoMarker™ FLM-di-Gal Figure 3. Coumarin based probes. (blue fluorescence)
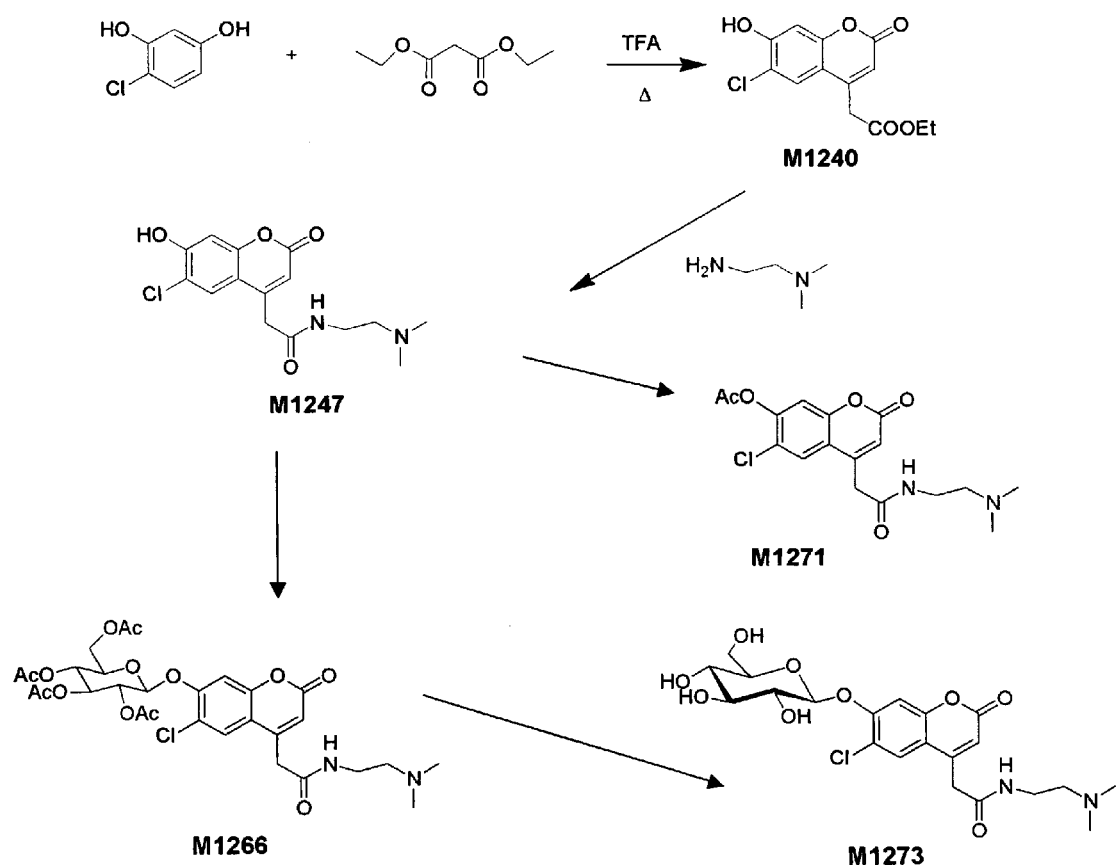

Figure 4. Naphthofluorescein – based probes.
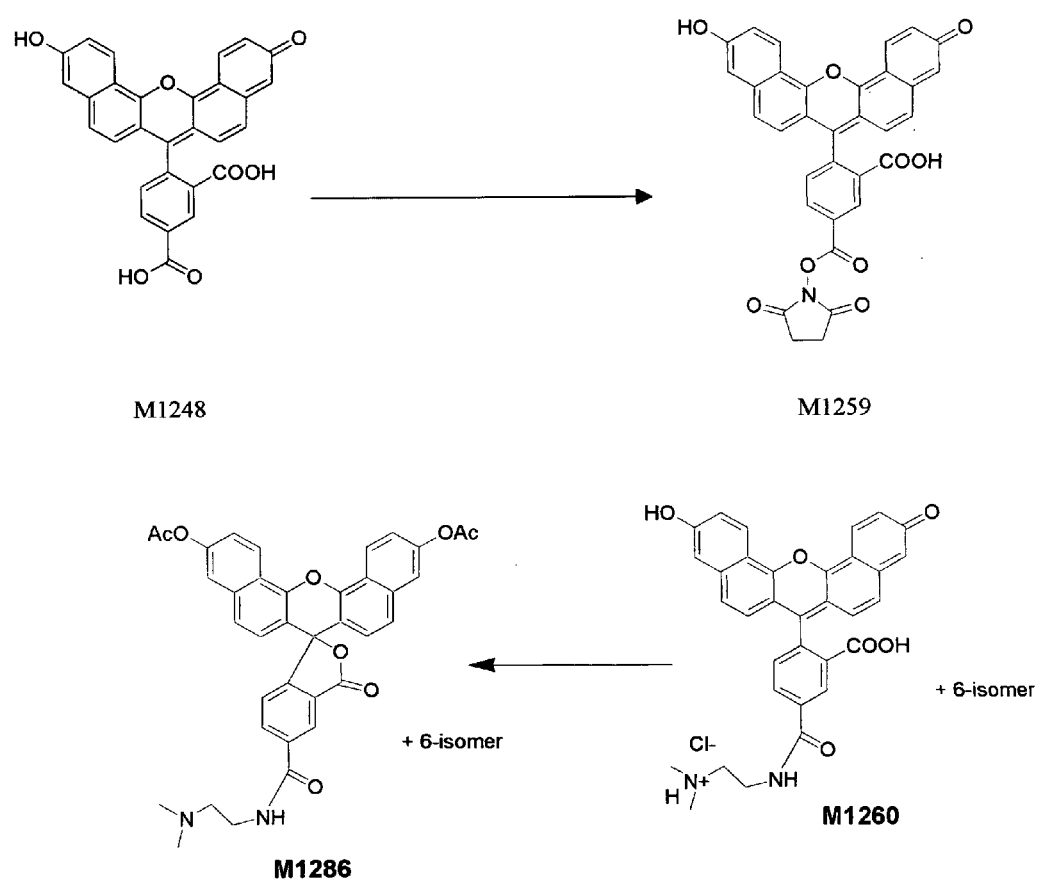

Figure 5. Benoxazoylumbelliferyl substrates. (with chloro group also)
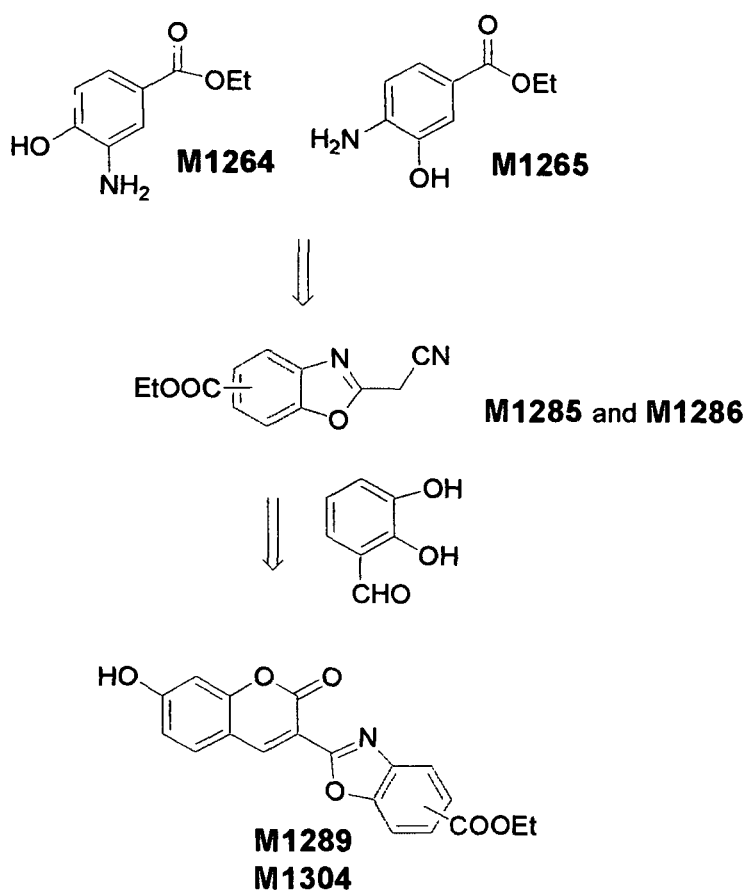

Figure 6: Benzoxazolylcoumarin Substrates.
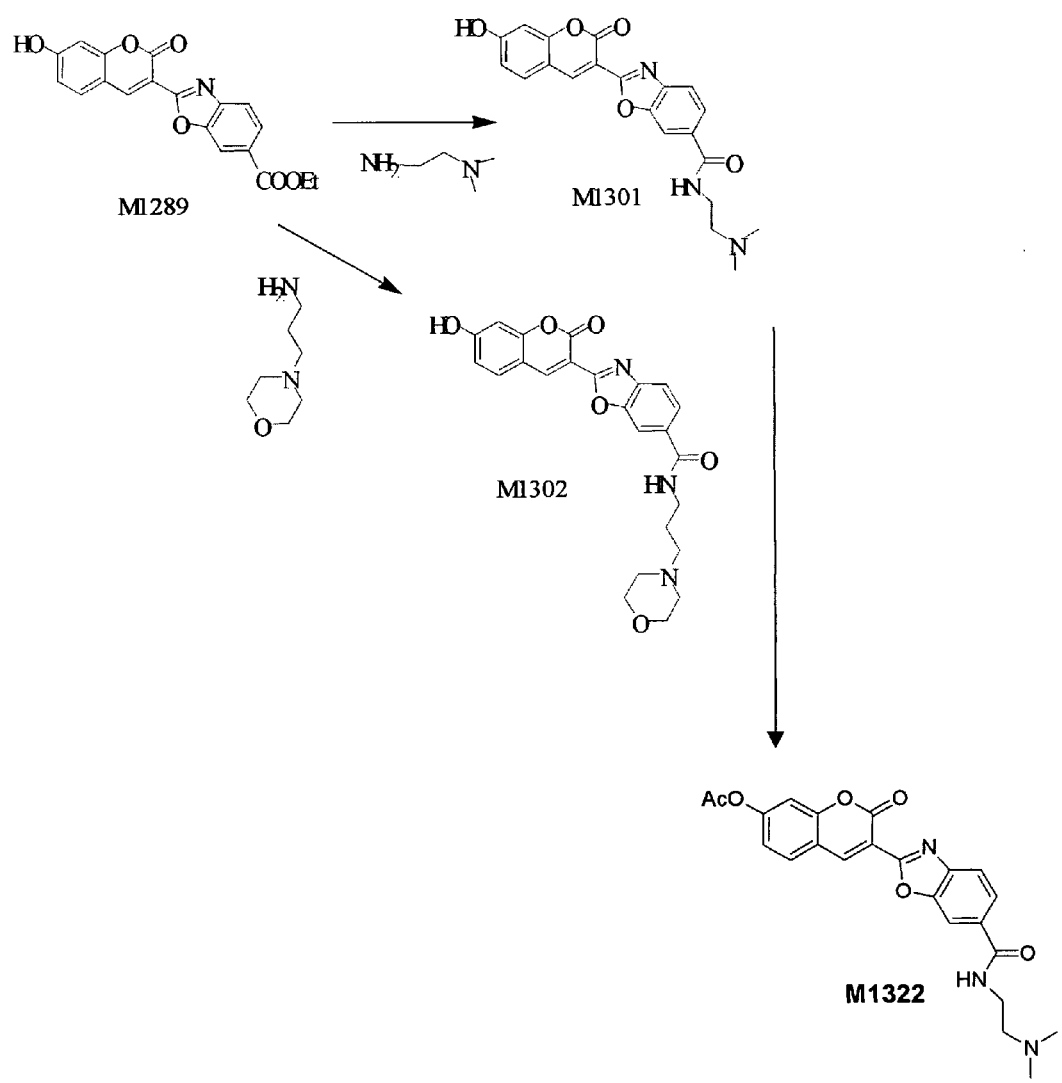

Figure 7. Gaucher Substrates based on M1247:
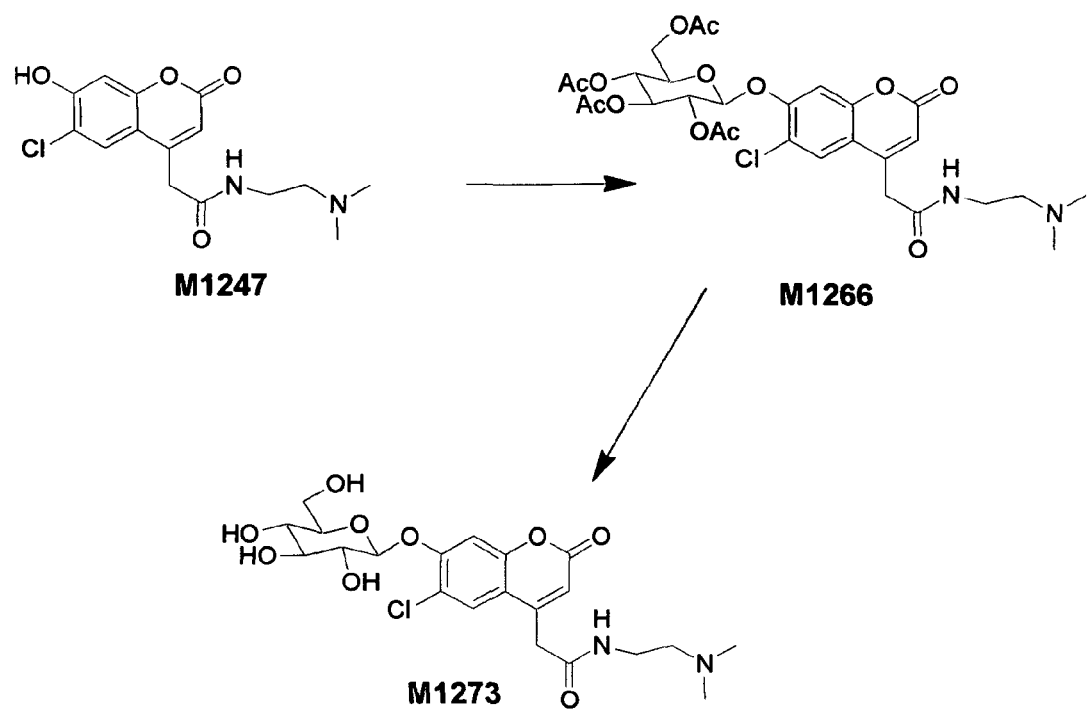

Figure 8. Lysosomal Targeted Esterase Substrates.
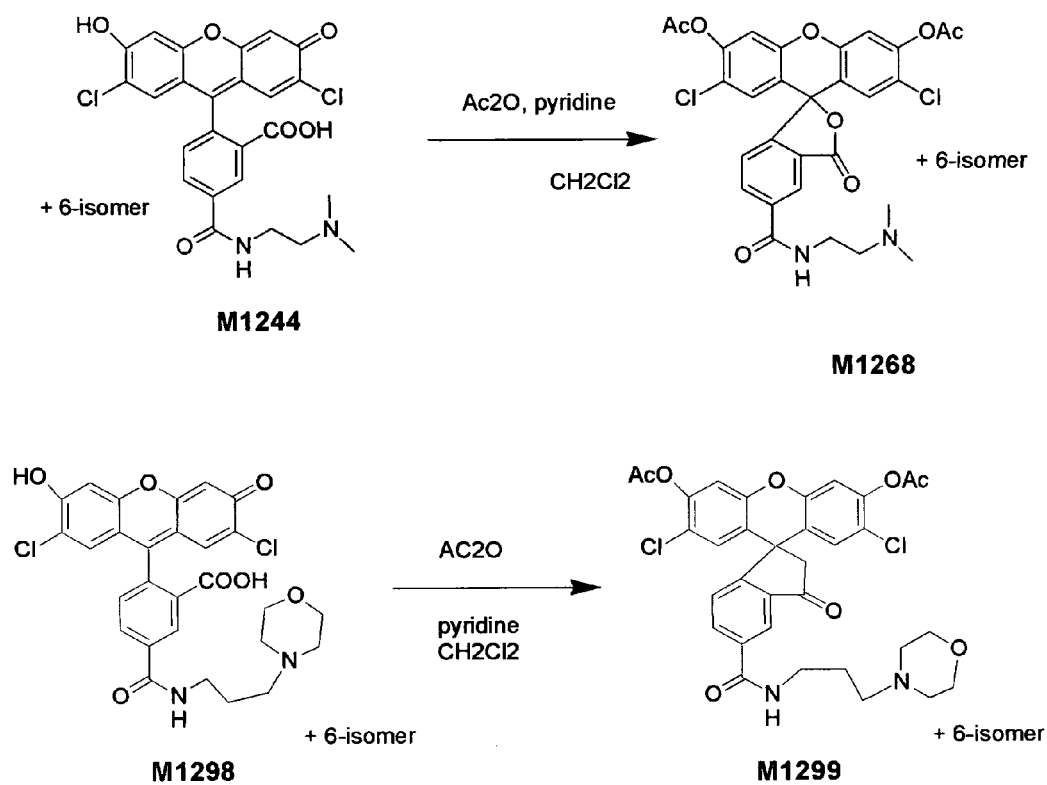

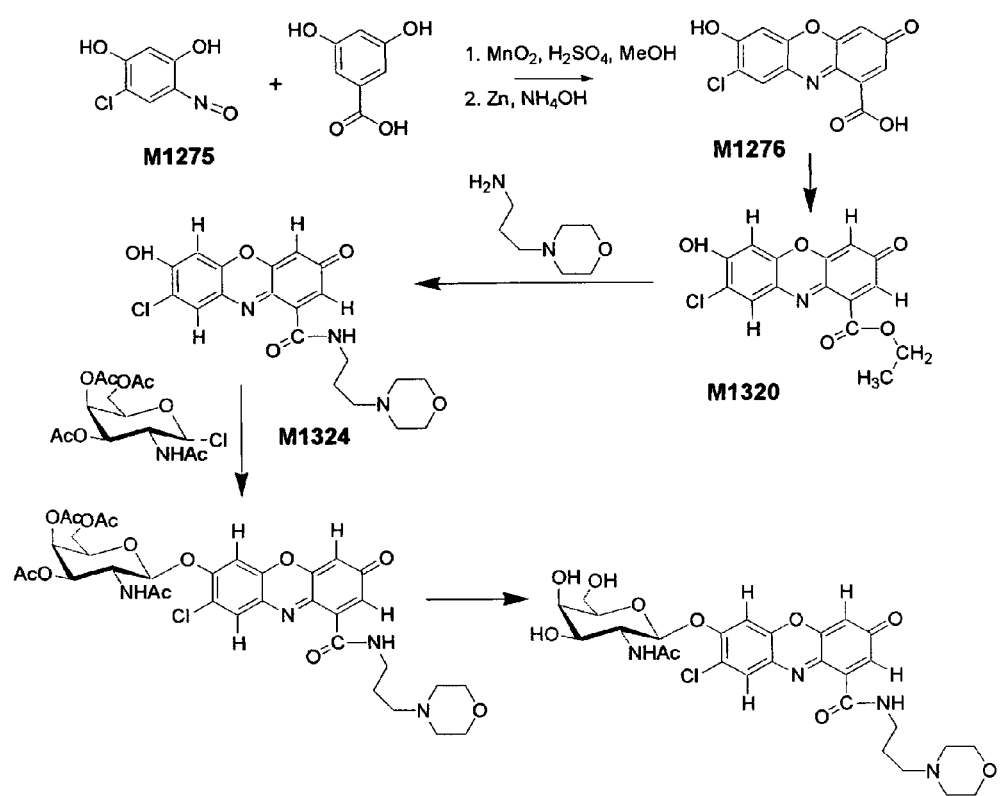
Figure 9. Hexosaminidase (Tay-Sachs) Lysosomal Targeted Substrates.

Figure 10: Lipophilic Targeting Group Esterase and Glycosidase Substrate Syntheses.
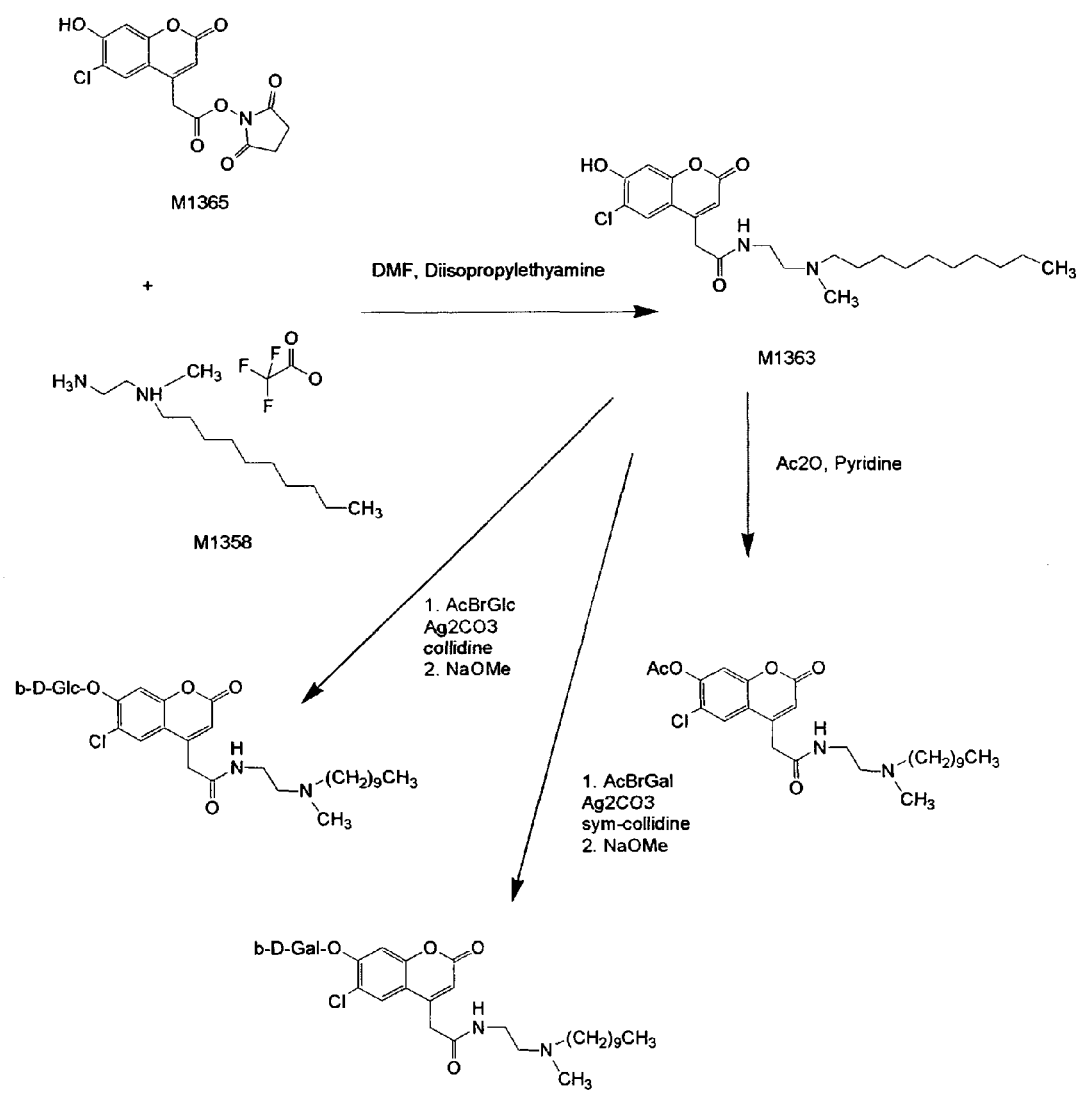

ENZYME SUBSTRATES FOR VISUALIZING ACIDIC ORGANELLES

This invention was made with Government support under grant 5R43MH079542-02 awarded by the National Institutes of Health. The Government has certain rights in this invention.

FIELD OF THE INVENTION

The present invention relates to the visualization of acidic organelles based upon organelle enzyme activity. The fluorescent organelle substrates of the invention are specific for enzyme activity of the organelle and label these organelles, such as lysosomes, rendering them fluorescent and easily observed.

BACKGROUND OF THE INVENTION

Acidic organelles are present in all cells and tissues of mammalian, plant, yeast and fungal cells, except red blood cells. Many bacteria also contain acidic compartments. These acidic organelles are often involved in metabolism and catabolism of foreign molecules that are brought into the cell by endocytosis. They are often the first line of defense against foreign bacterial or viral infection. The acidic pH of endosomes is critical to the process by which lipid-enveloped viruses enter the cytoplasm after their cellular uptake by receptor-mediated endocytosis. Phagocytosis is the process where extra cellular particles such as bacteria, are engulfed in the cell and then fused to lysosomes for digestion. Acidic organelles have also been shown to be responsible for digestion of high molecular weight proteins, oligosaccharides, glycolipids or peptides by the cell. In addition, they are often involved in therapeutic drug metabolism. Among the cellular organelles that have been found to mediate their enzyme activities by acidification are lysosomes, acidic endosomes, phagosomes, clathrin-coated vesicles and Golgi vescicles.

Lysosomes are an example of an acidic cytoplasmic organelle. Lysosomes have been found to be involved in a variety of cellular processes including repair of the plasma membrane, defense against pathogens, cholesterol homeostasis, bone remodeling, metabolism, apoptosis and cell signaling. To date, more than 50 acidic hydrolytic enzymes have been identified that are involved in ordered lysosomal degradation of proteins, lipids, carbohydrates and nucleic acids. Functional deficiencies in these lysosomal enzymes, however, are indicative of a number of disease states.

Many inherited carbohydrate metabolic diseases, especially lysosomal storage diseases, have been identified to date. These diseases include Hurler disease (MPS IH, i.e., mucopolysaccharidosis type IH), Scheie disease (NIPS IS), Hurler-Scheie disease (MPS I H/S), Hunter disease (MPS II), Sanfilippo disease (MPS III), Morquio disease (MPS IV), Maroteaux-Lamy disease (MPS VI), Sly disease (MPS VIII), mannosidosis, fucosidosis, sialidosis, asparylglycosaminuria, Gaucher disease (glucosylceramide lipidosis), Krabbe disease (galactoceramide-lipidosis), Fabry disease, Schindler disease, GM1 gangliosidoses, GM2 gangliosidoses, Tay-Sachs disease, Sandhoff disease, and mucolipidoses. As a group, these diseases are the most prevalent genetic abnormalities of humans. Gaucher disease, Sandhoff disease, Krabbé disease, and Tay-Sachs syndrome comprise the majority of patients in this category and are categorized as sphingolipidoses in which excessive quantities of undegraded fatty components of cell membranes accumulate because of inherited deficiencies of specific catabolic enzymes within lysosomes.

The therapeutic options for treating these diseases are relatively limited; in fact, there are currently no available therapies for many of these disorders. To date, therapeutic efforts have mainly focused on strategies for augmenting enzyme concentrations to compensate for the underlying defect. For this reason, new, sensitive and specific assays for monitoring lysosomal enzyme activities in living cells that will be of significant value in monitoring the success of current therapies and for discovery of new therapeutic strategies for diseases of lysosomal origin are needed.

Traditional lysosomal stains include the non-specific phenazine and acridine derivatives, neutral red and acridine orange, that are accumulated in the acidic vesicles upon being protonated. Fluorescently labeled latex beads and macromolecules, such as dextran, can also be accumulated in lysosomes by endocytosis in a variety of experiments.

Prior stains, methods and assays for visualizing acidic organelles such as lysosomes are not useful for monitoring lysosomal enzyme activities in living cells. For example, weakly basic amines have been shown to selectively accumulate in cellular compartments with low internal pH. When further linked to chromogenic or fluorogenic probes, they can be used to label these compartments. Among these is the frequently used acidotropic probe, N-(3-((2,4-dinitrophenyl)amino)propyl)-N-(3-aminopropyl)methylamine, dihydrochloride (hereafter referred to as DAMP). DAMP is not itself fluorescent and fixation and permeabilization of the cell, followed by the use of anti-DNP antibodies conjugated to a fluorophore, an enzyme or ferritin are required in order to visualize the staining pattern. The fluorescent dyes neutral red and acridine orange are also commonly used for staining acidic organelles, but they lack specificity and are not well retained in the organelles, particularly after fixing and permeabilization.

The compounds dansyl cadaverine and monodansyl cadaverine, which contain an aliphatic amino groups for targeting to the lysosome have been described as a lysosomotropic reagents. However, dansyl cadaverine is only described as having an effect on the function of human natural killer cells and human polymorphonuclear leucocytes. More recent research describes monodansyl cadaverine as a fluorescent label, however it is described as useful as a label for autophagic vacuoles, as it fails to label either endosomal compartments or lysosomes. In addition, the dansyl fluorophore is excited in the ultraviolet region (<350 nm), which is generally incompatible with living systems, has a low quantum yield and has a low extinction coefficient (less than 5,000) requiring high concentrations of dye when staining cells.

In addition, certain dipyrrometheneboron difluoride fluorophores linked to a weak base that is only partially protonated at neutral pH as described in U.S. Pat. No. 5,869,689, have been used for general labeling of lysosomes. But none of these probes are useful for monitoring specific enzyme activities in lysosomes or for metabolic analyses or analysis of enzyme activity defects.

Of the numerous lysosomal storage assay systems that have been reported, the majority utilize either fluorescent (4-methylumbelliferyl) substrates, chromogenic (nitrophenolic glycosides), glycolipids labeled with fluorescent dyes or radioactive substrates for detection of lysosomal glycosidase activities. These methods, however, utilize either cell lysate from cells or tissue homogenates, HPLC separation of enzymatic products and UV or fluorescent analysis or other complex analysis techniques. None of these assays, therefore, are well designed for an in vivo, or live-cell high-throughput systems detection, and require either biopsy or extensive cell preparation steps. In addition, the fluorescent dyes used in these assays are not amenable to the low pH environment of the lysosome and therefore do not allow imaging in the lysosome in its native environment. Accordingly, no methods have thus far been described that employ intact lysosomes or a live-cell format to monitor lysosomal enzyme activities.

SUMMARY OF THE INVENTION

The present invention includes methods and describes the synthesis of materials for analysis of acidic organelle enzyme activities, whether present in cells or in isolated cell-free organelle preparations, using substrates that produce a visible signal when acted upon by such enzymes. The method comprises: preparing a labeling solution containing an enzyme substrate or substrates of the present invention, where the labeling solution comprises a marker that produces a visible signal at low pH values and possessing a covalently attached basic amine moiety and is derivatized for specific enzyme analysis; and incubating with a sample comprising isolated acidic organelles, or live cells or tissues, allowing the labeling solution a sufficient time to produce labeling of the acidic organelles. Substrates of the present invention include substrates that produce a fluorescent signal. The use of the enzyme substrates of the invention are optionally combined with the use of additional detection reagents. The labeled cells are optionally observed using a means for detecting a fluorescent signal for microscopic analysis, fluorescence activated cell sorting or high-throughput screening analyses.

The fluorogenic acidic organelle enzyme substrates of this invention are designed to provide high fluorescence at low pH values and are derivatized to permit membrane permeation through both outer and organelle membranes of intact cells, can be used for staining cells at very low concentrations and are not toxic to living cells or tissues. The instant substrates and methods are useful for investigating metabolism, investigating the biogenesis of lysosomes, investigating the development of autophagic vacuoles, fusion of phagosomes with acidic lysosomes, investigating retina and cultured neurons, monitoring changes in lysosomal enzyme activities, monitoring enzyme activities associated with diseases, evaluating the relative levels of enzymes in both normal and diseased states and detecting pH gradients within lysosomes. In particular, the instant substrates and methods are useful for investigating lysosomal glycosidase activity, lysosomal peptidase activity, lysosomal aryl sulfatase activity, lysosomal lipase activity lysosomal phosphatase activity, lysosomal esterase activity. The current invention is also useful for labeling non-mammalian cells that possess acidic organelles, including yeast, spermatozoa and plant cells.

Among the enzymes that are present in acidic organelles and that can be detected using the substrates of the present invention are α-Mannosidase, β-Galactosidase, α-Galactosidase, β-Glucosidase, α-Glucosidase, b-Glucuronidase, β-acetylglucosaminidase, Neuraminidase, Hyaluronidase, Lipase, Phospholipase A, Esterase, Acid Phosphatase, Phospholipase C, Acid phospho-diesterase, Arylsulfatase A/B, Chondrosufatase, Lysozyme, β-Xylosidase, α- and β-Fucosidases, Cathepsin A, Acid Carboxy-Peptidase, Alanylaminopeptidase, Leucylaminopeptidase, Dipeptidase, Cathepsin B, Cathepsin H, Cathepsin L, Cathepsin C, Dipeptidyl Aminopeptidase II, Cathepsin D, Cathepsin E, Collagenase, Renin, Kininogen activator, Plasminogen activator, and Aspartylglucosyl aminidase. Those enzymes listed are given as a descriptive embodiment of the present invention but not intended to be a complete list of possible enzyme activities which may be detected using the substrates and methods of the present invention. Other enzymes which may be detected using the systems and substrates of the present invention will be obvious to a person skilled in the art.

BRIEF DESCRIPTION OF THE DRAWINGS

FIG. 1 shows fluorescein based staining probes of the present invention.
FIG. 2 shows Krabbe LysoMarker™ substrates of the present invention.
FIG. 3 shows coumarin based probes of the present invention.
FIG. 4 shows naphthofluorescein-based probes of the present invention.
FIG. 5 shows benoxazoylumbelliferyl substrates of the present invention.
FIG. 6 shows benzoxazolylcoumarin substrates of the present invention.
FIG. 7 shows Gaucher substrates based on M1247 of the present invention.
FIG. 8 shows lysosomal targeted esterase substrates of the present invention.
FIG. 9 shows hexosaminidase (Tay-Sachs) lysosomal targeted substrates of the present invention.
FIG. 10 shows lipophilic targeting group esterase and glycosidase substrate syntheses of the present invention.

DESCRIPTION OF THE PREFERRED EMBODIMENTS

The present invention utilizes fluorogenic, chromogenic or chemiluminescent enzyme substrates for the labeling and tracing of acidic organelles in cells and cell-free systems. These new substrates selectively accumulate in cellular compartments with low internal pH and can be used to investigate the enzyme levels responsible for biosynthesis, degradation and recycling of cellular components and for measuring specific enzyme defects involved in a number of human diseases linked to enzyme activity in lysosomes within live cells.

The acidic organelle substrates of the present invention have the general formula

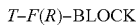

$T\text{-}F(R)\text{-}BLOCK$

Where T represents a Targeting group that is a weakly basic amine containing compound that partitions the substrate to the acidic organelle or lysosome, F represents a reporter that provides a visible signal upon the removal of BLOCK that has further elaboration with substituent or substituents R to provide for fluorescence at low pH values, and BLOCK represents a biological molecule including a carbohydrate, amino acid, peptide, phosphate, sulfate, lipid or nucleic acid group that can be removed by specific enzyme activity within the acidic organelle or lysosome, thus allowing F to provide a visible signal.

In a particular embodiment, acidic organelle substrates of the present invention have the general formula:

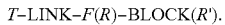

$T\text{-}LINK\text{-}F(R)\text{-}BLOCK(R')$.

In this embodiment, the LINK portion of LINK-T is a covalent linkage, serving to attach a weakly basic amine, T, to the reporter, F. Any suitable covalent linkage that does not interfere with the ability of the substrate to selectively accumulate in acidic organelles is an acceptable covalent linkage for the purposes of the present invention. In one embodiment, LINK is a single covalent bond. Preferred LINK groups have 1-20 nonhydrogen atoms selected from the group consisting of C, N, O and S. Such LINK groups are composed of any combination of chemical bonds, including ether, thioether, amine, ester, carboxamide, sulfonamide, hydrazide bonds, and single, double, triple carbon-carbon bonds, and aromatic or heteroaromatic bonds. Preferred LINK groups are composed of any combination of single carbon-carbon bonds and carboxamide bonds. Selected specific examples of LINK optionally include methylenes, oligomethylenes, phenylenes, thienyls, carboxamides, and sulfonamides. In one embodiment of the invention, LINK contains 1-6 carbon atoms. In an additional embodiment of the invention, LINK has the formula —$(CH_2)_a(CONH(CH_2)_b)_z$—, where a has any value from 0-5, b has any value from 1-5 and z is 0 or 1.

In this embodiment BLOCK group can be further modified with a substituent or substituents (R') that improve membrane permeability of the substrate through cellular membranes.

The substituent or substituents R, which may be the same or different, are selected from the group hydrogen, halogen, cyano, alkyl, substituted methane, perhalogenated alkyl, perfluoroalkyl, halomethyl, alkoxy, cycloalkyl, arylalkyl, acyl, aryl, heteroaryl, alkenyl or alkynyl; or a LINK-T moiety.

Preferably, the substituent or substituents R that are not a LINK-T moiety include electron-withdrawing groups such as, halogen, cyano, alkyl, aryl, heteroaryl, alkenyl or may be a hydrogen. More preferably, the substituent or substituents R that are not a LINK-T are halogen, aryl or cyano. Alternatively, for those substrates where R is linked to a fused aromatic 6-membered ring that is optionally and independently substituted once or more, at any position, by halogen, cyano, alkyl, perfluoroalkyl, alkoxy, alkenyl, alkynyl, cycloalkyl, alkylthio, alkylamido, amino, monoalkylamino, dialkylamino, carboxamide, hydroxy, mercapto, aryl, heteroaryl, aryl-amido, heteroaryl-amido, aryl-oxy, heteroaryl-oxy, aryl-amino, or heteroaryl-amino, or 1-2 additional fused benzo or heteroaromatic rings that are themselves optionally further substituted by halogen, amino or carboxamide. Any of the fused aromatic 6-membered rings or additional fused benzo or heteroaromatic rings is optionally substituted one or more times by a LINK-T moiety.

As used herein, aryl is an aromatic or polyaromatic substituent containing 1 to 4 aromatic rings (each ring containing 6 conjugated carbon atoms and no heteroatoms) that are optionally fused to each other or bonded to each other by carbon-carbon single bonds. Each aryl is bound by a single bond, and is optionally substituted as described below.

As used herein, a heteroaryl is an aromatic group that contains at least one heteroatom (a non-carbon atom within the ring structure). Each heteroaryl is a single 5- or 6-member ring, or is a fused 2- or 3-ring structure. The heteroaryl group contains one or more heteroatoms, e.g. as pyrrole, thiophene, or furan (single ring, single heteroatom), or oxazole, isoxazole, oxadiazole, or imidazole (single ring, multiple heteroatoms), or benzoxazole, benzothiazole, or benzimidazole (multi-ring, multiple heteroatoms), or benzofuran or indole (multi-ring, single heteroatom). Each heteroaryl is bound by a single bond, and is optionally substituted as described below.

Any aryl, heteroaryl, aryl-amido, heteroaryl-amido, aryl-oxy, heteroaryl-oxy, aryl-amino or heteroaryl-amino substituent is optionally and independently substituted one or more times by halogen, amino, carboxamide, hydroxy or mercapto.

Any of said alkenyl or alkynyl substituents independently has 2-6 carbons, and is optionally substituted by halogen, alkyl, cyano, carboxylate ester, carboxamide, aryl, heteroaryl, or additional alkenyl or alkynyl groups. Preferably an alkenyl group is an ethenyl, dienyl or trienyl group.

Each of the alkyl substituents, as well as the alkyl portions of alkoxy, cycloalkyl, arylalkyl, alkylamino, alkylthio or alkylamido substituents independently has 1-6 carbons, and is optionally substituted by halogen, amino, alkylamino, dialkylamino, carboxamide, hydroxy, mercapto or cyano.

In a particular embodiment, at least one of R substituents is a LINK-T moiety, a LINK-T substituted methine, or one of the F substituents that is a fused 6-membered ring is further substituted by a LINK-T moiety. For all embodiments, where F is substituted by more than one LINK-T, they are the same or different.

The targeting group T has the general formula —$CR_cR_d$—$NR_eR_f$. The substituents $R_c$ and $R_d$ are independently hydrogen or alkyls having 1-6 carbons that are linear or branched. Typically, $R_e$ and $R_f$ are hydrogen or alkyls having 1-16 carbons, more preferably $R_e$ is methyl and $R_f$ is either methyl, alkyl having 2-16 carbons, or are part of a nitrogen heterocyclic ring system such as morpholine, piperidine, pyrrolidine, piperazine, imidazole, oxazepine, azepine or pyrrole. Where $R_e$ or $R_f$ are alkyl groups, each alkyl group is optionally further substituted by halogen, carboxamide, oxy, hydroxy, mercapto or cyano. In addition, any alkyl group is optionally further substituted by a primary, secondary or tertiary amine, where the alkyl groups present on the amine independently have 1-6 carbons. In an additional embodiment of the invention, one of $R_e$ and $R_f$, when taken in combination with the LINK moiety, forms a five- to eight-membered ring.

The amine substituents $R_e$ and $R_f$ are each independently H or a linear or branched alkyl having 1-6 carbons. Alternatively, $R_e$ and $R_f$, when taken in combination form a $R_e$ and $R_f$ that preserves the basic nature of the amine nitrogen. Preferably, the nitrogen heterocycle is a pyrrolidine, a piperidine, a piperazine, morpholine, an imidazole, an azepine (including diazepines and triazepines) or an oxazepine. In another embodiment of the invention, the amine substituents $R_e$ and $R_f$, when taken in combination with substituents $R_c$ and $R_d$, or with the LINK moiety, form a saturated five- or six-membered nitrogen heterocycle that is a substituted pyrrolidine or piperidine.

For all embodiments of the invention, the basic targeting group moiety T is optionally present in the form of a salt of a strong acid, for example a hydrochloride salt, sulfate salt, perchlorate salt, or other organic acid salts.

Selected specific embodiments of substrates useful for the staining of acidic organelles and lysosomes are described in FIGS. 1 through 10.

The substrates and probes of the present invention are readily prepared using the methods described herein. Specific methods for preparing the covalent linkage, LINK, and Targeting Group T are demonstrated in the Examples.

Compounds wherein the LINK or T moiety incorporates a cyclic structure are prepared by reaction of a preformed reactive reporter (F) with an appropriate amine-containing intermediate, or by preparing amine-containing pyrroles prior to formation of the reporter.

The substrates of the invention are only partially protonated at neutral pH. The spectral properties of the probe can be tuned over a wide range of the visible and near infra-red spectrum through selection of the substituents as described herein, making them especially useful for multicolor applications. Similarly, selection of substituents allow the pH selectivity of the substrate to be tuned for specific applications. For example, a substrate having a Targeting moiety T that is less basic will be protonated by more acidic conditions, and therefore more selectively accumulate at locations having a lower pH.

The substrates of the present invention are freely permeant to cell membranes, and typically selectively accumulate in acidic organelles. The staining characteristics are generally not reversed or are only partially reversed by subsequent treatment of the cells with additional weakly basic cell-permeant compounds. Accordingly, staining may be preserved even after fixation and/or permeabilization of the cells.

The substrates of the present invention are utilized by preparing a labeling solution containing one or more of the substrates of the present application, introducing the labeling solution into the sample containing or thought to contain acidic organelles, incubating the sample for a time sufficient to produce a detectable visual signal, and observing or analyzing the staining pattern in the sample. The sample may be a cell or cells that contain acidic organelles or the sample may contain isolated acidic organelles (i.e. not incorporated in a cell), or the sample may be two solutions separated by a semi-permeable membrane.

The degree of staining of acidic organelles is a reflection of the pH gradient present across the acidic organelles membrane at the time of staining, i.e., the degree of staining is indicative of whether or not the organelle is acidic at the time of staining. While the substrates of the present invention are typically used for staining the acidic organdies of live cells, the present invention is also useful for staining isolated (i.e. cell-free) acidic organelles, provided the organelles are not disrupted and a pH gradient still exists between the organelle and the medium in which it is suspended. While in general the presence of acidic organelles can be considered an indicator of cell viability, it is possible to render a cell non-viable, while still retaining acidic organelles in the sample.

Furthermore, the substrates of the present invention can be made from fluorescent dyes that have the property of modifying their fluorescence spectrum as a function of pH upon enzyme turnover. Among the REPORTER dyes that exhibit changes in signal dependent upon the pH environment at the site of activity are the courmarins, fluoresceins, naphthfluoresceins, carbocyanines and rhodamines.

The pure substrates of the present invention may have low solubility in water. Typically a stock solution is prepared by dissolving a known mass of the pure substrate in an organic solvent. Preferred organic solvents are DMSO, DMF, N-methylpyrrolidone, acetone, acetonitrile, dioxane, tetrahydrofuran, methanol or ethanol or other completely water-miscible solvents. Alternatively, the substrate is dispersed in a water immiscible solvent or oil, or is evaporated from an organic solvent leaving a thin film. The labeling solution is prepared by diluting an aliquot of the stock solution into an aqueous or partially aqueous buffer to the desired labeling concentration. In one embodiment of the invention, two or more substrates of the invention are present in the labeling solution, having similar or distinct spectral properties.

In general the amount of substrate added in the labeling solution is the minimum amount required to yield detectable staining of the acidic organelles present in the sample within a reasonable time, with minimal background staining or staining of other organelles or cellular structures. The amount of substrate required for staining eukaryotic cells depends on the sensitivity required for staining the intracellular acidic organelles, the number of cells present, the permeability of the cell membrane to the substrate, and the time required for the probe to localize to the organelles. The required concentration for the labeling solution is determined by systematic variation in labeling concentration until a satisfactory fluorescent labeling is accomplished. Typically, the amount of substrate required for staining animal cells is 10 to 200 uM, preferably below 500 uM.

Low concentrations of substrate require longer incubation times for equivalent fluorescent brightness to be reached. Typically cells incubated in 10 uM labeling solution require about 2 hours to reach an arbitrary level of staining that is reached in about 30 minutes using a 200 uM labeling solution. For those embodiments where the acidic organelles to be stained are vacuoles present in plant cells, yeast or other fungal cells, a higher concentration of substrate is used, due to the lower permeability of the plant, yeast or other cell membranes. Typically, when staining fungal cells, a substrate concentration of 1 mM is satisfactory to give good vacuolar staining.

Staining concentrations less than about 100 uM give good staining of acidic organelles in live animal cells. At higher concentrations of stain, background fluorescence increase in live cells, but resolution of acidic organelles after fixation is improved. Staining of isolated (cell-free) acidic organelles typically requires lower concentrations of substrates.

The exact concentration of substrates to be used is dependent upon the experimental conditions and the desired results and optimization of experimental conditions is required to determine the best concentration of stain to be used in a given application. Such conditions and concentrations needed for optimal staining can be readily discerned by one of skill in the art in view of the present disclosure.

The sample optionally comprises cell-free acidic organelles or cells that contain acidic organelles. Any cells that contain acidic organelles can be used, including but not limited to, fresh or cultured cells, cell lines, cells in biological fluids, cells in tissue or biopsy, yeast cells, plant cells and sperm cells. Where the sample contains cells, the cells are optionally abnormal cells, such as tumor cells or other cancer cells, where the abnormal cells are present in vitro or in vivo, or primary cells derived from patients with specific disease. Acidic organelles of interest that are stained using the present method of staining include, but are not limited to, lysosomes, phagovacuoles, endosomes, yeast vacuoles and acrosomes. In one embodiment of the invention, the staining method is used to label all lysosomal compartments in the sample. Typically, the acidic organelles that are stained are lysosomes or acrosomes. More typically, the acidic organelles that are stained are lysosomes.

Most plant and fungal cells (including the unicellular fungi and yeast) contain one or more very large, fluid-filled vesicles called vacuoles. In yeast, the vacuoles typically occupy more than 70% of the cell volume. Yeast vacuoles are related to lysosomes of animal cells, and contain a variety of hydrolytic enzymes with an acidic pH in the lumen.

The sample is typically stained by passive means; that is the labeling solution is combined with the sample being analyzed. The substrates of the present invention are introduced into the sample organelles by incubation of the sample in the labeling solution. Where the sample contains a cell or cells, the cells are similarly stained by incubation of the cell or cells in the labeling solution. Alternatively, the sample is stained by direct uptake of the substrate from a thin film of the substrate applied to a plate, microplate or cell well. Any other method of introducing the substrates into the sample cell, such as microinjection of a labeling solution, can be used to accelerate introduction of the substrates into the cellular cytoplasm. Typically the substrates will be introduced into the sample cell by incubation in the labeling solution, or by microinjection. Preferably the substrate is introduced to the sample by incubation in the labeling solution. Microinjection of substrate solution is used when labeling of the acidic organelles in a single cell is desired, within a colony of other sample cells.

A number of reagents and conditions are known to affect the pH gradient of acidic organelles, and therefore the staining by the substrates of the invention, including but not limited to nutrients (for example carbohydrates such as glucose) and selected drugs.

The substrates of the present invention are generally nontoxic to living cells and acidic organelles. Sample cells have been incubated in 200 uM substrate solution for 72 hours without observable ill effects. Stained cells have been observed to undergo cell division, producing daughter cells that also possess stained acidic organelles.

Optionally, the cells or isolated acidic organelles are washed to improve the results of the staining procedure. Washing the sample cell or cells after incubation in the labeling solution, or optionally after fixation or permeabilization, greatly improves the visualization of the acidic organelles. This is largely due to the decrease in non-specific background staining after washing. Satisfactory visualization of acidic organelles is possible without washing by using low labeling concentrations (for example <50 nM).

The sample can be observed immediately after staining of acidic organelles becomes evident. After staining, the cells or isolated acidic organelles in a sample are optionally fixed. Selected embodiments of the substrates described above are well retained in cells, and sample cells stained with these substrates retain considerable visual staining after fixation. A number of fixatives and fixation conditions are suitable for practicing this invention. Useful fixatives include, but are not limited to, formaldehyde, paraformaldehyde, formalin, glutaraldehyde, cold methanol and 3:1 methanol acetic acid. Typically, cell fixation is accomplished by incubating the stained cells in a 3.7% solution of paraformaldehyde for about 15-30 minutes. Fixation is typically used to preserve cellular morphology and to reduce biohazards when working with pathogenic samples.

Fixation is optionally followed or accompanied by permeabilization, such as with acetone, ethanol, DMSO or various detergents. Permeabilization is utilized to allow bulky additional detection reagents to enter the cellular space that would ordinarily be impermeant to an intact cellular membrane. A large variety of fixatives, fixation conditions, and permeabilization agents are known in the art, and other methods of fixing or permeabilizing sample cells in conjunction with the stains of the present invention will be obvious to one of ordinary skill.

The use of the acidic organelle substrates of the present invention is optionally combined with the use of an additional detection reagent. An additional detection reagent is a reagent that produces a detectable response due to the presence of a specific cell component, intracellular substance, or cellular condition. One or more additional detection reagents may be used in conjunction with the substrates of the present invention, before or after fixation and/or permeabilization. The additional detection reagent may be used to stain the entire cell, or a cellular substructure. The visual signal of the acidic organelle substrates of the present invention and the detectable response of the additional detection reagent may be observed simultaneously or sequentially. The observation of acidic organelle staining and a detectable response that are spatially coincident indicate that the additional detection reagent is associated with the acidic organelles. A variety of measurements can be made within acidic organelles in this manner, even when the additional detection reagent does not itself localize selectively within the acidic organelles.

One class of appropriate additional detection reagents are fluorescent nucleic acid stains. A wide variety of appropriate nucleic acid stains are known in the art, including but not limited to, Thiazole Orange, ethidium homodimer, propidium iodide, Hoechst 33258, and DAPI. Additional useful nucleic acid stains are known to those of skill in the art. The use of an appropriate nucleic acid stain in conjunction with the substrates of the present invention can be selected to allow simultaneous observation of acidic organelles, nuclear DNA, cellular RNA and/or mitochondrial DNA. Of particular utility is an additional detection reagent that is a cell-permeant nucleic acid stain, allowing simultaneous visualization of acidic organelles and the cell nucleus.

Other appropriate additional detection reagents include selected fluorescent metal ion indicators described in U.S. Pat. No. 5,453,517 to Kuhn et al. (1995), or U.S. Pat. No. 5,405,975 to Kuhn et al. (1995).

In another embodiment of the invention, an appropriate additional detection reagent is any probe that selectively stains a cellular organelle such as the cell membrane, nucleus, Golgi apparatus, mitochondrion, endoplasmic reticulum, or is a second acidic organelle probe.

Specific examples of additional detection reagents include mitochondria-targeted stains, such as Rhodamine 123. Additional fluorescent stains specific for mitochondria are described in U.S. Pat. No. 5,459,268 to Haugland et al. (1995). The above mitochondrial stains accumulate in mitochondria, and are fixable therein, allowing simultaneous visualization of both mitochondria and acidic organelles in fixed and permeabilized cells.

In one embodiment, the additional detection reagent comprises: a) one member of a specific binding pair or a series of specific binding pairs, and b) a means for producing a detectable response. A specific binding pair member can be a ligand or a receptor. As used in this document, the term ligand means any organic compound for which a receptor naturally exists or can be prepared. A receptor is any compound or composition capable or recognizing a spatial or polar organization of a molecule, e.g. epitopic or determinant site. Ligands for which naturally occurring receptors exist include natural and synthetic peptides and proteins, including avidin and streptavidin, antibodies, enzymes, and hormones; nucleotides and natural or synthetic oligonucleotides; lipids; polysaccharides and carbohydrates; lectins; and a variety of drugs, including therapeutic drugs and drugs of abuse and pesticides. Ligands and receptors are complementary members of a specific binding pair, each specific binding pair member having an area on the surface or in a cavity which specifically binds to and is complementary with a particular spatial and polar organization of the other.

The additional detection reagent may be used in conjunction with enzyme conjugates to localize cellular receptors; to localize hybridization probes; or to probe cells and tissues that do not express the enzyme, for example, by enzyme-linked immunosorbent assay (ELISA), or enzyme-mediated histochemistry or cytochemistry, or other enzyme-mediated techniques. Enzyme-mediated techniques take advantage of the attraction between specific binding pairs to detect a variety of analytes. In one embodiment, the additional detection reaction comprises an enzyme substrate to produces a fluorescent precipitate in the presence of the appropriate enzyme, as described in U.S. Pat. No. 5,316,906 to Haugland et al. (1994) and U.S. Pat. No. 5,443,986 to Haugland et al. (1995).

In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a "complementary conjugate". Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

The additional detection reagent also incorporates a means for producing a detectable response. A detectable response means a change in, or occurrence of, a parameter in a test system which is capable of being perceived, either by direct observation or instrumentally, and which is a function of the presence of a specifically targeted member of a specific binding pair in a cell sample. Such detectable responses include the change in, or appearance of, color, fluorescence, reflectance, pH, chemiluminescence, infrared emission, or the deposition of an electron-rich substrate. Appropriate labels to provide a detectable response include, but are not limited to, a visible or fluorescent dye, an enzyme substrate which produces a visible or fluorescent precipitate upon enzyme action (for example, the action of horseradish peroxidase upon diaminobenzidine), visible or fluorescent labeled latex microparticles, or a signal that is released by the action of light upon the reagent (e.g. a caged fluorophore that is activated by photolysis, or the action of light upon diaminobenzidine).

At any time after or during staining, the sample is observed with a means for detecting a visual signal present in the stained acidic organelles. For example, when using a substrate of the present invention that produces a florescent visual signal, the sample is illuminated with a wavelength of light that results in a detectable fluorescence response. In one embodiment of the invention, the fluorescently labeled organelles are observed after the cell or cells have additionally been fixed and/or permeabilized. Observation is accomplished using visible light microscopy, or alternatively, observation of the sample comprises illuminating the stained sample with a wavelength of light appropriate to generate a fluorescent response, and visually examining the sample by use of a microscope, or confocal microscope.

The sample is optionally illuminated at a wavelength of ultraviolet, visible or infrared light specific for optimal excitation of a fluorophore present in the sample after enzyme action to remove the BLOCK group. Where the sample contains more than one BLOCK, or contains an additional detection reagent, illumination occurs at a wavelength that generates a detectable fluorescence response in each fluorescent substrate or additional detection reagent, where said substrates and detection reagents possess overlapping excitation maxima.

Typically, the substrates of the invention typically possess a strong absorbance at visible wavelengths, typically at greater than 450 nm, preferably at greater than 500 nm, yet more preferably at greater than 600 nm. The preferred substrates of the invention exhibit an extinction coefficient greater than 10,000/cm M, preferably at greater than 30,000/cm M. The fluorophores of the invention typically possess quantum yields of fluorescence emission that are greater than 0.3, preferably greater than 0.7.

Optionally, the sample is observed using instrumentation. For example, where the sample contains a cell or cells, observation of the sample is accomplished by illuminating the stained cell or cells with a wavelength of light appropriate to generate a fluorescent response, and electronically detecting and optionally quantifying the fluorescent emission of the stained acidic organelles using an appropriate instrument, such as a fluorescence microscope equipped with a digital camera, fluorometer, fluorescent microplate reader, or a flow cytometer.

The observation of the fluorescent response of the sample optionally includes selecting or sorting the acidic organelles based upon their fluorescent response. Typically the sample comprises cells having stained acidic organelles, and the cells of the sample are sorted based upon the staining of the individual cells. The step of sorting is typically accomplished using a flow cytometer or a fluorescence microscope.

The use of simple fluorescent dyes as sensitizing agents to enhance photodynamic therapy (PDT) has been described by Boyer (U.S. Pat. No. 5,189,029) and Morgan (U.S. Pat. No. 5,446,157). Photodynamic therapy refers to the process wherein illumination is utilized to destroy cells, typically abnormal cells, that have previously been labeled with a dye. Several references, including Geze, et al. (Photochem. Photobiol. 20, 23-35 (1993)) and Berg et al. (Int. J. Cancer 59, 814-822 (1994)) have previously indicated that the photolysis of dyes that are localized to lysosomes destroys tumor cells. Furthermore, the lysosomes of tumor cells are generally considered to have a lower pH than normal lysosomes ("Molecular Aspects of Anticancer Drug Action", Neidel and Waring, Eds., Macmillan, London; pp 233-286 (1983)). Selective uptake of PDT dyes into tumor cells in preference to normal cells is an important property allowing selective photodestruction of abnormal cells in the course of PDT treatment, while minimizing the destruction of normal cells.

The method of the current invention has utility for photodynamic therapy, as described above, as the greater acidity of lysosomes in tumor cells, will result in greater uptake of the acidotropic substrates in tumor cells. Photolysis of the stained cells will then result in destruction of the target tumor cells without affecting neighboring normal cells and tissues. Although cells and tissues stained according to the present method are potential PDT targets, preferably the long wavelength fluorescent dyes used for PDT targeting of cells are those that absorb beyond 600 nm, more preferably those that absorb beyond 650 nm, due to the enhanced penetration of light through tissue at these wavelengths. Particularly preferred are the substrates of the invention having fused aromatic substituents that are further substituted by a LINK-T moiety. Additional preferred substrates of the invention for PDT are those having bromine or iodine substituents.

Preferred substrate concentrations for labeling cells for PDT are those concentrations that have been determined to produce the greatest selective uptake of substrate into abnormal cells without detriment to normal cells, such that photolytic activity is maintained in the abnormal cells. As described above, micromolar concentrations of substrate are effective in staining acidic organelles of live cells. The substrates are applied to cells for PDT by means well understood in the art, including local or systemic injection, topical application, incorporation into liposomes or other means. substrate uptake into cells is by passive diffusion or receptor-mediated uptake. Selective accumulation in lysosomes is facilitated by the pH gradient that favors uptake into the more acidic organelles. Photolysis is performed with any excitation source that is capable of producing light that can be absorbed by the substrate, including lasers and light sources that produce infrared irradiation. This light may be delivered either directly to the cells that contain the substrate, or delivered indirectly such as through an optical fiber. Fluorescence properties of the substrate can be used to guide and determine which cells are to be irradiated.

The examples below are given so as to illustrate the practice of this invention. They are not intended to limit or define the entire scope of this invention.

Example 1

Preparation of a Lysosomal β-Galactosidase Substrate with Green Fluorescence after Enzyme Reaction The following compound was prepared:

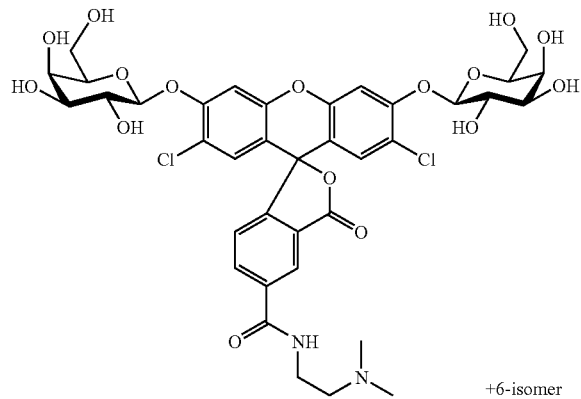

5(6)-(2-dimethylaminoethyl)carboxamido)-2'7'-dichlorofluorescein

To a dry 100 mL round bottom flask under anhydrous $N_{2(g)}$ was added N-hydroxysuccinimide (5.75 g, 50 mmol), dissolved in trifluoroacetic anhydride (20.0 mL, 144 mmol) and allowed to stir at room temperature for 1.5 h. This reaction mixture was rotary evaporated under reduced pressure and co-evaporated with dry toluene (3×20 mL) at 50° C. and dried in vacuo to give O-trifluoroacetyl-N-hydroxysuccinimide as a white amorphous crystalline solid (10.57 g, 100%).

Under anhydrous conditions, a sample of O-trifluoroacetyl-N-hydroxysuccinimide (10.57 g, 50 mmol) was dissolved in anhydrous DMF (20 mL) and 5(6)-carboxy-2',7'-dichlorofluorescein (5.20 g, 12 mmol) and dry pyridine (10.0 mL, 130 mmol) were added. This mixture was allowed to stir at room temperature under anhydrous conditions overnight. The reaction mixture was then poured into ice-water (300 mL) with stirring and extracted with ethylacetate (200 mL). The aqueous layer was extracted again with ethylacetate (100 mL) and the combined ethylacetate layers were washed with water (200 mL) and brine solution (200 mL), dried over anhydrous sodium sulfate, filtered, evaporated and dried in vacuo to give a bright orange amorphous solid (4.65 g, 84%). Chromatography (TLC: $SiO_2$ plate, 7:3 ethylacetate:methanol irrigant, $R_f$=0.53 and 0.79) indicated approximately a 1:1 mixture of the two isomeric active esters.

A sample of the above NHS-esters (4.65 g, 10.1 mmol) was dissolved in anhydrous DMF (50 mL) and unsym-dimethyl-ethylenediamine (1.65 mL, 15 mmol) added. This mixture was allowed to stir under anhydrous conditions, at room temperature overnight. Ethylacetate (200 mL) was added with stirring for 30 min. and the pale orange precipitate filtered, washed with ethylacetate and dried in vacuo to give the title dimethylaminoethyl amides (2.88 g, 57%). The combined ethylacetate filtrates from above were extracted with 1 N HCl/H2O solution (2×100 mL) and the resulting aqueous layers washed with dichloromethane (2×25 mL), evaporated to dryness and the resulting orange oil was triturated with diethylether to give a second crop of the title compound (as the HCl-salt form) (2.20 g, total yield=97%).

5(6)-(2-dimethylaminoethyl)carboxamido)-2',7'-dichlorofluorescein-3',6'-di-O-β-D-galactopyanoside, octaacetate A sample of 5(6)-(2-dimethylaminoethyl)carboxamido)-2'7'-dichlorofluorescein (3.20 g, 6.37 mmol) was suspended in anhydrous dichloromethane (40 mL), THF (40 mL) and anhydrous acetonitrile (20 mL). To this solution was added acetobromogalactose (6.76 g, 16.4 mmol), dry silver carbonate (2.20 g, 7.96 mmol) and sym-collidine (2.0 mL, 15.1 mmol), the flask covered in Al-foil (darkness) and allowed to stir under anhydrous $N_{2(g)}$ for 72 h. Additional acetobromogalactose (5.5 g) and silver carbonate (1.75 g) were added and left the reaction to continued stirring as above for 18 h. The reaction mixture was filtered through a Celite™ pad and the silver salts washed with excess dichloromethane. The filtrates were combined and evaporated to a brown oil, redissolved in dichloromethane (100 mL) and washed with water (100 mL), 1 N HCl solution (100 mL) saturated sodium bicarbonate solution (2×100 mL) 1 N HCl solution (2×100 mL) and brine (100 mL). The resulting dichloromethane layer was dried over anhydrous sodium sulfate, filtered and applied to a column of silicagel 60 (70-230 mesh, 100×45 mm) and eluted using a gradient elution method of dichloromethane:ethylacetate (0-20%). Fractions containing the second major product to elute from the column were combined and evaporated to give an off-white foam (2.52 g, 34%).

5(6)-(2-dimethylaminoethyl)carboxamido)-2'7'-dichlorofluorescein-3',6'-di-O-β-D-galactopycmoside To a flame dried 250 mL one-neck, round-bottom flask under dry $N_{2(g)}$ was added 5(6)-(2-dimethylaminoethyl)carboxamido)-2'7'-dichlorofluorescein-3',6'-di-O-β-D-galactopyanoside, octaacetate (1.50 g, 3.0 mmol). The sample was suspended in anhydrous methanol (100 mL), cooled to 0° C. (ice-bath) under an atmosphere of dry nitrogen gas and 25% (w/v) sodium methoxide/methanol solution (1.0 mL, 250 mg) added with stirring. The solution was allowed to react under anhydrous conditions for 3 hours at 0° C., warmed to room temperature and neutralized with washed, dry IRC50 (H+) resin (2 grams). The resin was filtered and washed with methanol, and the combined filtrates evaporated to dryness and dried in vacuo to an off white solid (1.05 grams, 98%). Crystallization from methanol:diethylether (1:10, 2×) gave a product homogeneous by TLC analysis (7:3 ethylacetate:methanol irrigant; Rf=0.08).

Example 2

Preparation of an Esterase Substrate with Blue Fluorescence Emission upon Enzyme Activity The following compound was prepared:

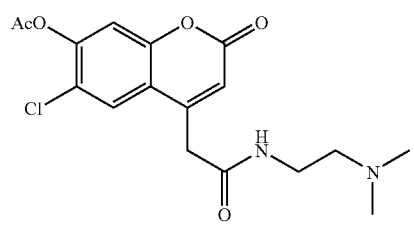 [SMILES: CC(=O)Oc1cc2oc(=O)cc(CC(=O)NCCN(C)C)c2cc1Cl]

To a flame dried 50 mL round-bottom flask under an atmosphere of dry $N_2$(g) was weighed 3-(2'-dimethylaminoethylcarboxamidomethyl)-6-chloro-7-hydroxycoumarin (M1247, 99 mg, 0.3 mmole). This sample was suspended in anhydrous dichloromethane (20 mL), cooled to 0° C. (ice-bath) and acetic anhydride (1.0 mL, 10.6 mmole) and dry pyridine (1.0 mL, 12.4 mmole) added. The reaction was allowed to stir at 0° C. for 2 hours and at room-temperature overnight. The reaction mixture was diluted with dichloromethane (30 mL) and poured into ice-water (100 mL) with stirring. The organic layer was separated and washed with saturated sodium bicarbonate solution (1×100 mL) and brine solution (1×100 mL), dried over anhydrous sodium sulfate, filtered, evaporated and co-evaporated with dry toluene (2×10 mL) to give a clear glass (50 mg, 42%) homogeneous by TLC analysis (irrigant 9:1 dichloromethane:methanol; Rf=0.85).

Example 3

Preparation of a Lipase Substrate with Green Fluorescence Upon Enzyme Activity

The following compound was prepared:

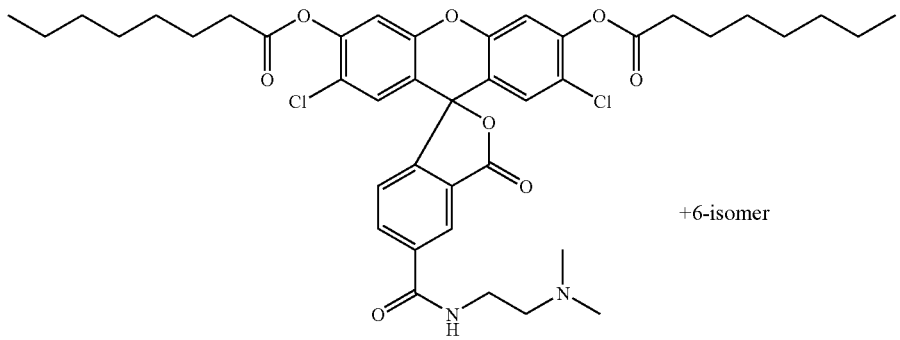 [SMILES: CCCCCCCC(=O)Oc1cc2c(cc1Cl)C1(OC(=O)c3cc(C(=O)NCCN(C)C)ccc31)c1cc(Cl)c(OC(=O)CCCCCCC)cc1O2]

5(6)-(2-dimethylaminoethyl)carboxamido)-2'7'-dichlorofluorescein, di-O-octanoate 5(6)-(2-dimethylaminoethyl)carboxamido)-2'7'-dichlorofluorescein (152 mg, 0.295 mmole) was suspended in anhydrous dichloromethane (10 mL) and cooled to 0° C. (ice-bath) while under anhydrous conditions under dry nitrogen gas. To this solution was added octanoyl chloride (250 uL, 1.62 mmole) and dry pyridine (1120 uL, 14.42 mmole) and the reaction mixture was placed in an ultrasonic bath for 30 min. to complete dissolution of the starting materials. This reaction mixture was allowed to react at ambient temperature under anhydrous conditions overnight. The reaction was diluted with dichloromethane (50 mL) and poured into ice-water (50 mL), extracted, and the resulting organic layer washed with ice-water (1×50 mL), saturated sodium bicarbonate solution (1×50 mL) 1 N HCl solution (1×50 mL) and brine solution (1×50 mL), dried over anhydrous sodium sulfate, filtered, evaporated and dried in vacuo to give a clear tan oil (184 mg, 81%). TLC analysis showed two spots of essentially equal intensity for the two isomeric 5(6)-derivatives at Rf=0.42 and 0.48 (irrigant=9:1 CH$_2$Cl$_2$:MeOH). $^1$H-NMR (d$_6$-DMSO) (mixture of 5 and 6-isomers) δ: 9.1 (m, 0.5H); 9.0 (m, 0.5H); 8.5 (s, 0.5H); 8.2 (m, 0.5); 8.1 (m, 0.5H); 8.0 (d, 0.5H); 7.8 (s, 0.5H); 7.6 (m, 0.5H); 7.6 (s, 1H); 7.5 (d, 0.5H); 7.4 (d, 0.5H); 7.2 (s, 0.5H); 7.1 (s, 0.5H); 3.7 (m, 1H), 3.6 (m, 1H); 3.3 (m, 1H), 3.2 (m, 1H); 2.4 (2, 6H); 1.6 (m, 4H); 1.3 (br. s, 20H); 1.8 (t, 6H).

Example 4

Preparation of a β-Glucosidase Substrate with Blue Fluorescence Upon Enzyme Activity The following compound was prepared:

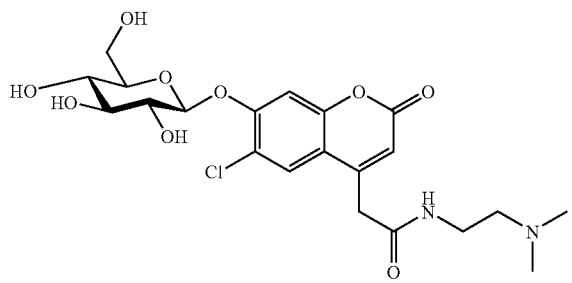

+6-isomer

3-Acetoxyethyl-6-chloro-7-hydroxycoumarin

To a flame-dried 50 mL round-bottom flask is weighed 4-chlororesorcinol (1.44 g, 10 mmole) and diethyl-1,3-acetonedicarboxylate (1.82 mL, 10 mmole) and trifluoroacetic acid (10.0 mL) added. This mixture is heated to reflux (98° C.) in an oil-bath for 18 hours, cooled to room-temperature and poured into ice-water (100 mL) with stirring for 1 hour. The resulting off-white precipitate is filtered and washed with ice-cold water, dried in air and in vacuo overnight to give a yellow crystalline powder (1.29 g, 4.56 mmole, 46%) TLC (irrigant=7:3 ethylacetate:methanol, Rf=0.86).

3-(2'-dimethylaminoethylcarboxamidomethyl)-6-chloro-7-hydroxycoumarin

To a dry 50 mL round-bottom flask was weighed 3-Acetoxyethyl-6-chloro-7-hydroxycoumarin (500 mg, 1.77 mmole) and unsym-dimethylethylenediamine (5 mL, 45.38 mmole) added. This mixture was heated with stirring to reflux for 2 hours and at room-temperature overnight, evaporated and co-evaporated with dry toluene (4×25 mL) and dried in vacuo overnight. The resulting reddish oil was triturated repeatedly with anhydrous diethylether to give a tan powder (0.58 g, 100%) homogeneous by TLC analysis (1:1 ethylacetate:methanol) (Rf=0.10). $^1$H-NMR (d$_6$-DMSO) δ: 8.2 (br. s, 1H, NH); 7.8 (d, 1H); 6.6 (d, 1H); 6.0 (d, 1H); 3.5 (m, 2H); 3.1 (m, 2H); 2.1 (s, 6H).

7-O-(2,3,4,6-tetra-O-acetylβ-D-glucopyranosyl)-6-chloro-3-(2 dimethylaminoethylcarboxamidomethyl)coumarin Under anhydrous conditions, 3-(2'-dimethylaminoethyl-carboxamidomethyl)-6-chloro-7-hydroxycoumarin (354 mg, 1.09 mmole) was suspended in anhydrous dichloromethane (20 mL) containing 3 A molecular sieve (0.5 g) and anhydrous acetonitrile (10 mL), acetobromoglucose (686 mg, 1.66 mmole), sym-collidine (500 uL, 3.78 mmole) and dry silver carbonate (247 mg, 0.9 mmole) added. This mixture was allowed to react under anhydrous nitrogen in the dark for 72 hours at room temperature. The reaction mixture was filtered through a Celite™ pad and the greenish precipitate washed with excess dichloromethane. The combined filtrates were extracted with brine solution (2×100 mL), saturated sodium bicarbonate solution (1×100 mL), 0.2 N sodium thiosulfate solution (1×100 mL) and brine solution (1×100 mL), dried over anhydrous sodium sulfate, filtered and evaporated to dryness. The product was purified on a 20×20 cm preparative TLC plate (1 mm thickness) with elution using 8:2 dichloromethane:acetonitrile as eluent. The highest Rf band was removed from the plate, eluted with 1:1 dichloromethane:acetonitrile as solvent, filtered and dried in vacuo to give the title compound (126 mg) homogeneous by TLC analysis.

7-O-β-D-glucopyranosyl-6-chloro- 3-(2'-dimethylaminoethylcarboxamidomethyl) coumarin A sample of 7-O-(2,3,4,6-tetra-O-acetyl-β-D- glucopyranosyl)-6-chloro-3-(2'-dimethylaminoethylcarboxamidomethyl)coumarin (113 mg, 0.17 mmole) was suspended in anhydrous methanol (15 mL) under dry nitrogen gas, and 25% sodium methoxide in methanol solution (800 uL, 200 mg NaOMe) added. This mixture was allowed to stir under anhydrous conditions for 6 hours, neutralized with washed, dry IRC50 (H+) resin (0.5 g) and filtered. The resin was washed with fresh methanol and the combined filtrates evaporated and dried in vacuo overnight to a clear oil which was triturated with anhydrous diethylether (25 mg) to give a white solid (58 mg, 69%). TLC (7:3 ethylacetate:methanol irrigant showed one spot, Rf=0.75). $^1$H-NMR ($d_6$-DMSO) δ: 7.8 (s, 1H); 7.5 (s, 1H); 6.3 (s, 1H); 5.2 (d, 1H, H-1); 4.9-4.0 (m, 4H, —OH); 3.6-2.8 (m, 10H, CHO ring and targeting arm protons); 2.4 (s, 6H, —$CH_3$'s).

Example 5

Preparation of an Arylsulfatase Substrate with Green Fluorescence Emission Upon Enzyme Activity The following compound was prepared:

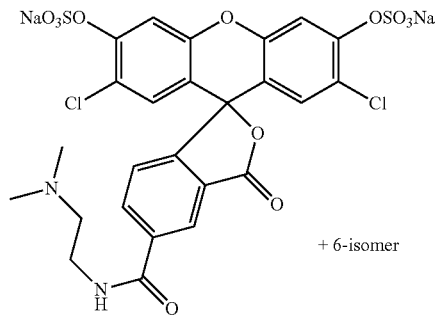

+ 6-isomer

5(6)-(2-dimethylaminoethyl)carboxamido)-2'7'-dichlorofluorescein disulfate, disodium salt A solution of 5(6)-(2-dimethylaminoethyl)carboxamido)-2'7'-dichlorofluorescein (66 mg, 0.128 mmoles) was dissolved in anhydrous pyridine (5.0 mL) under anhydrous $N_{2(g)}$, cooled to 0° C. (ice-bath) and chlorosulfonic acid (43 mg, 0.64 mmole) added dropwise with stirring. This solution was allowed to react at 0° C. for 2 hours and at room-temperature overnight. The solution was evaporated under reduced pressure (T<40° C.) and co-evaporated with dry toluene (2×30 mL), dried briefly in-vacuo and treated with 0.1 mM NaOH solution (6.4 mL) and the resulting solution applied to a column of Sephadex LH-20 resin, with elution using water. Fractions containing the quenching non-fluorescent product were combined and lyophilized to give a light tan solid (46 mg, 50%). TLC (irrigant=9:1:1 dichloromethane:methanol:acetic acid) Rf=0.0 originally quenching, but fluorescent upon H+ treatment.

Example 6

Preparation of an Acid Phosphatase Substrate with Green Fluorescence Upon Enzyme Activity The following compound was prepared:

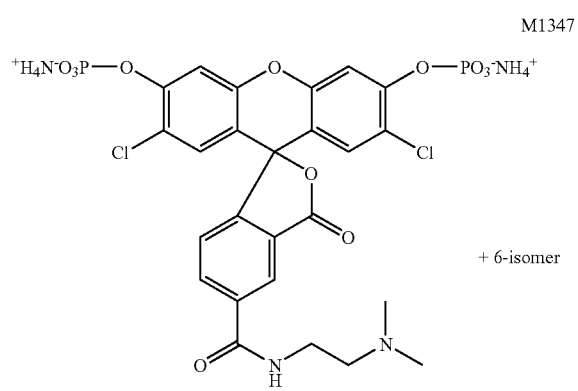

M1347

+ 6-isomer

5(6)-(2-dimethylaminoethyl)carboxamido)-2'7'-dichlorofluorescein diphosphate, diammonium salt A solution of 5(6)-(2-dimethylaminoethyl)carboxamido)-2'7'-dichlorofluorescein (76 mg, 0.147 mmoles) was dissolved in anhydrous pyridine (2.5 mL) under anhydrous $N_{2(g)}$, and was cooled to 0° C. (ice-bath) and phosphorous oxychloride (100 uL, 1.07 mmole) added slowly with stirring. This mixture was allowed to stir at 0° C. for 2 hours and at room-temperature for 18 hours. The reaction mixture was centrifuged, and the orange solid redissolved in ice-water (20 mL) and neutralized with dilute ammonium hydroxide solution (pH 8). The resulting solution was lyophilized, and applied to a column of Sephadex G-10 and eluted with water. Fractions containing the first quenching product to elute from the column were combined, lyophilized to give a pale yellow solid, that was triturated with methanol and redried to give the title compound (33 mg, 34%). TLC analysis (3:3:6:1 CH2CL2:MeOH:H2O:HOAc) (Rf=0.2) (quenching, non-fluorescent until acid treatment).

Example 7

Preparation of an Esterase Substrate with Green Fluorescence after Enzyme Activity The following compound was prepared:

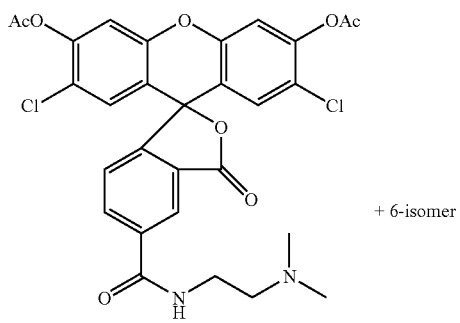

M1268

+ 6-isomer

5(6)-(2-dimethylaminoethyl)carboxamido)-2'7'-dichlorofluorescein diacetate

A suspension of 5(6)-(2-dimethylaminoethyl)carboxamido)-2'7'-dichlorofluorescein (101 mg, 0.20 mmole) in anhydrous dichloromethane (20 mL) was cooled to 0° C. (ice-bath) and acetic anhydride (1.0 mL, 10.6 mole) and dry pyridine (1.0 mL, 12.4 mmole) was added. This mixture was allowed to stir at 0° C. for two hours and at ambient temperature overnight. The reaction mixture was diluted with dichloromethane (100 mL) poured into ice-water (100 mL), extracted and the organic layer washed with ice-cold saturated sodium bicarbonate solution (100 mL), water (100 mL) and brine solution (200 mL). The resulting organic layer was dried over anhydrous sodium sulfate filtered, evaporated and dried in vacuo to give a pale tan solid that was triturated with diethyl ether, centrifuged, decanted and the off-white crystals dried in vacuo (40 mg, 33%). TLC analysis (9:1 $CH_2Cl_2$: MeOH) showed a two spots Rf=0.58 and 0.42) $^1$H-NMR ($d_6$-DMSO) (5 and 6 isomers) δ: 8.7 (t, 0.5H); 8.6 (t, 0.5H); 8.3 (s, 0.5H); 8.0 (d, 0.5H); 7.9 (m, 0.5H); 7.5 (s, 0.5H); 7.2 (d, 0.5H); 6.8 (s, 1H); 6.4 (s, 1H); 3.2 (m, 2H); 3.1 (m, 2H); 2.5 (s, 6H, —CH3's); 2.1 (s, 6H, —OAc's).

Example 8

Preparation of an Esterase Substrate Containing a Morpholino Targeting Group with Green Fluorescence after Enzyme Activity The following compound was prepared:

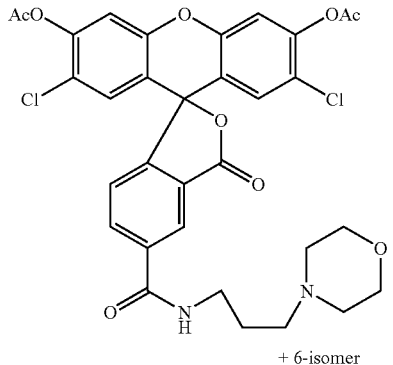 [SMILES: CC(=O)Oc1cc2c(cc1Cl)C1(OC(=O)c3cc(C(=O)NCCCN4CCOCC4)ccc31)c1cc(Cl)c(OC(C)=O)cc1O2]

+ 6-isomer

5(6)-(3-N-morpholinopropyl)carboxamido)-2'7'-dichlorofluorescein

O-trifluoroacetyl-N-hydroxysuccinimide (11.18 g, 53 mmol) was dissolved in anhydrous dimethylformamide (20 mL) and 5(6)-carboxy-2',7'-dichlorofluorescein (5.20 g, 12.0 mmole) added, with stirring. This mixture was allowed to stir at room temperature under anhydrous conditions for 12 hours after which time, TLC analysis (mini-workup with ethylacetate:water; ethylacetate layer; irrigant=7:3 ethylacetate:water) indicated that the reaction was complete. The reaction mixture was then poured into ice-water (300 mL) with stirring and extracted with ethylacetate (200 mL). The layers were separated and the aqueous layer washed again with ethylacetate (100 mL). The combined ethylacetate layers were washed with water (200 mL), brine solution (200 mL), 1 N HCl/$H_2O$ (200 mL) and brine (100 mL). A significant amount of orange precipitate formed which was filtered and dried (1.79 g, appears to be a single isomer, by TLC analysis (7:3 ethylacetate:methanol; Rf=0.5). The filtrate was dried over anhydrous sodium sulfate, filtered, evaporated and dried in vacuo to give a bright orange solid (TLC analysis (7:3 ethylacetate:methanol irrigant), 2 isomers, Rf=0.53 and 0.79) (4.65 g, 6.44 g total yield 70%). A sample of the mixed isomeric NHS esters (1.00 g, 2.17 mmole) was dissolved in anhydrous DMF, and 3-aminopropyl-N-morpholine (1.3 mL, 8.90 mmole, 4.1 equiv.) added with stirring. This mixture was allowed to stir under anhydrous conditions overnight, evaporated under vacuum to a bright red oil (1.53 g) that was triturated with ethyl acetate (50 mL) (30 min.) and diethyl ether (50 mL) (overnight) to remove excess morpholino compound. The product was filtered and redissolved in dry methanol, evaporated and dried overnight in vacuo to give an orange solid (542 mg, 44%) homogeneous by TLC analysis (irrigant=7:3 ethylacetate:methanol) Rf=0.06).

5(6)-(3-N-morpholinopropyl)carboxamido)-2'7'-dichlorofluorescein diacetate

The sample of 5(6)-(3-N-morpholinopropyl)carboxamido)-2'7'-dichlorofluorescein (542 mg, 0.95 mmole) was dissolved in anhydrous dichloromethane (10 mL) and acetic anhydride (1.0 mL, 10.6 mmole) and dry pyridine (1.0 mL, 12.4 mmole) added. This reaction mixture was allowed to stir overnight under anhydrous conditions. The reaction mixture was then diluted with dichloromethane (50 mL) and poured into ice-water (150 mL) with stirring. After stirring for 30 min. to destroy excess acetic anhydride, the layers were separated and the organic layer was with ice-cold saturated sodium bicarbonate solution (25 mL), 1 N HCl solution (25 mL) and water (25 mL). The organic layer was dried over anhydrous sodium sulfate, evaporated and dried in vacuo to a clear, pale tan oil, homogeneous by TLC analysis (irrigant=9:1 dichloromethane:methanol; Rf=0.58 and 0.55) as two closely separated isomers, quenching at UV 254 nm, but non-fluorescent. A biocompatible staining solution was prepared by dissolving 86 mg of the above compound in anhydrous DMSO (1.312 mL) to give a 100 mM solution.

Example 9

Preparation of a β-Galactosidase Substrate with Green Fluorescence after Enzyme Activity and a Morpholino Targeting Group The following compound was prepared:

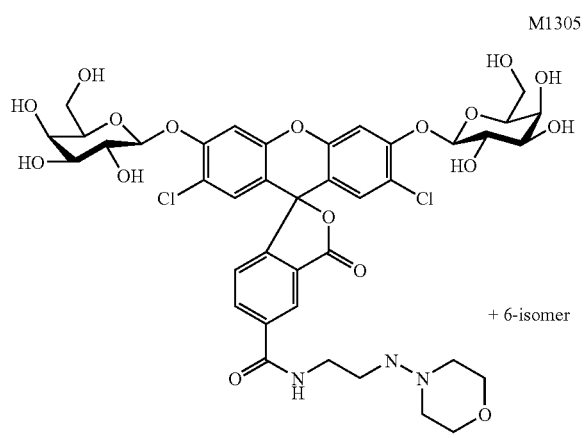

5(6)-(3-N-morpholinopropyl)-carboxamido)-2'7'-dichlorofluorescein di-β-D-Galactopyranoside, octaacetate A sample of 5(6)-(3-N-morpholinopropyl)-carboxamido)-2'7'-dichlorofluorescein (1.60 g, 2.80 mmole) was dried in vacuo overnight, placed under anhydrous $N_{2(g)}$, and acetobromogalactose (2.90 g, 7.0 mmole, 2.5 equiv.) added. These solids were suspended in anhydrous dichloromethane (15 mL) and anhydrous acetonitrile (15 mL) and solid, dry silver carbonate (970 mg, 3.5 mmole), sym-collidine (930 uL, 7.0 mmole), dry 3 A molecular sieves (1 g) were added. This reaction mixture was covered in Al-foil (darkness) and allowed to stir under anhydrous conditions for 3 days. After this time, the reaction mixture was filtered through a bed of diatomaceous earth (Celite™ 545) and the precipitate washed with excess dichloromethane. The combined filtrates were washed with water, saturated aqueous sodium bicarbonate solution, 1 N HCl, 0.2 N sodium thiosulfate solution and water (each 1×100 mL). The organic layer was dried over anhydrous sodium sulfate, filtered, evaporated to a low volume and applied to a slurry-packed column of silicagel 60 (70-230 mesh, 125 g, 40×160 mm) prepared in dichloromethane. The product was eluted by gradient elution, using dichloromethane (500 mL), 8:2 dichlorormethane:ethylacetate (1.5 L), 7:3 dichloromethane:ethylacetate (500 mL), 6:4 dichloromethane:ethylacetate (500 mL) and 9:1 dichloromethane:methanol (500 mL). Fractions containing the first major quenching (UV 254 nm) product to elute from the column were combined, evaporated and dried in vacuo to give a clear oil (540 mg, 16%). TLC (8:2 dichloromethane:ethylacetate, Rf=0.13). $^1$H-NMR ($d_6$-DMSO) (mixture of 5 and 6 isomers) δ: 8.4 (d, 0.5H); 8.3 (m, 0.5H); 8.2 (s, 0.5H); 7.8 (s, 0.5H); 7.6 (d, 0.5H); 7.2-6.9 (m, 4.5H); 6.1 (d, 2H, H-1); 5.4-5.0 (m, 6H); 4.5 (m, 2H); 4.2-3.9 (8H); 2.4 (s, 4H); 2.1-1.9 (4s, 24H); 1.2 (t, 2H).

5(6)-(3-N-morpholinopropyl)-carboxamido)-2'7'-dichlorofluorescein di-1'-D-Galactopyranoside A sample of 5(6)-(3-N-morpholinopropyl)-carboxamido)-2'7'-dichlorofluorescein di-(3-D-galactopyranoside, octaacetate (540 mg, 0.44 mmole) was dried in vacuo overnight, placed under anhydrous $N_{2(g)}$ and dissolved in anhydrous methanol (40 mL). To this solution was added 25% (w/v) sodium methoxide in methanol (90 mg, 1.66 mmole) and this mixture allowed to stir under anhydrous conditions for 2.5 hours. The reaction mixture was then neutralized with washed, dry IRC-50 (H+) resin, allowing the resin to stir for about 30 min. The resin was filtered and washed with excess dry methanol, evaporated to a low volume (about 5 mL) (rotary evaporator, T<35° C.) and crystallized by adding dry diethylether (100 mL). The solution was stored at 4° C. overnight to complete crystallization, and the off-white crystals filtered and washed with fresh diethylether to give an off-white crystalline solid (190 mg, 48%). TLC analysis (irrigant=9:1:1 dichloromethane:methanol:acetic acid, Rf=0.05). The solid was very hygroscopic and difficult to weigh. Biocompatible solutions of the product were prepared in DMSO for cell staining experiments. $^1$H-NMR ($d_6$-DMSO) (5 and 6 isomers) δ: 8.4 (d, 0.5H); 8.3 (m, 0.5H); 8.2 (d, 0.5H); 7.8 (s, 0.5H); 7.5 (d, 0.5H); 7.2 (s, 2H); 7.0 (s, 0.5H); 6.9 (s, 2H); 6.5 (d, 2H); 6.1 (d, 2H, H-1); 5.1 (m, 2H, H-4); 5.2-4.2 (m, 10H); 3.9-3.2 (20H); 2.5 (t, 4H); 1.0 (t, 2H).

Example 10

Preparation of an Esterase Substrate with Red Fluorescence after Enzyme Activity The following compound was prepared:

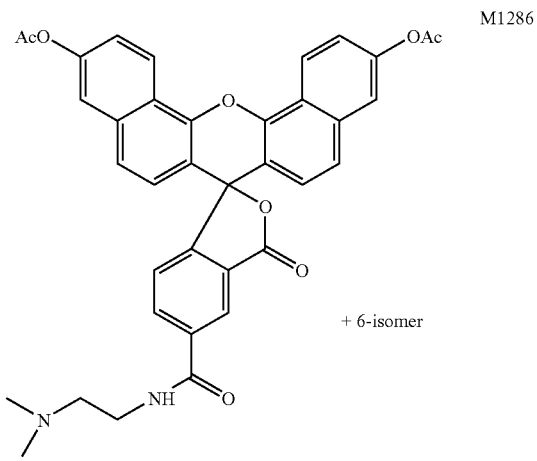 [SMILES: CC(=O)Oc1ccc2c3c(ccc2c1)C1(OC(=O)c2cc(C(=O)NCCN(C)C)ccc21)c1ccc2cc(OC(C)=O)ccc2c1O3]

5(6)-Carboxynaphthofluorescein

To a dry 300 mL round-bottom flask was added trimellitic anhydride (9.60 g, 50 mmole), 1,6-dihydroxynaphthalene (16.02 grams, 100 mmole) and fused zinc chloride (11.60 grams, 85.1 mmole). These solids were mixed manually and heated to 180° C. (oil-bath) neat, overnight. The reaction was cooled to room-temperature and the purple solid digested with 4 N NaOH solution (150 mL), filtered to remove zinc salts and the precipitate washed with water. The filtrate was cooled to 0° C. (added DI-ice) and neutralized with concentrated HCl (~30 mL) to pH 3. The resulting dark red sample was stored at 4° C. overnight to complete crystallization, filtered and the dark red solid washed with water until the filtrate was neutral. The solid was dried in air and in vacuo overnight to give a dark red powder (43 g). Repeated attempts to recrystallize the sample were unsuccessful. An 8.0 gram sample of the above crude product was dissolved in methanol (50 mL) containing triethylamine (TEA, 1 mL), and adsorbed to Celite™ 545 (about 10 grams), evaporated and dried in vacuo. This sample was applied to a slurry packed column of silicagel 60 (70-230 mesh) (250 grams, 45×300 mm) and eluted by gradient elution with 9:1 dichloromethane:methanol (1.5 L), 9:1 dichloromethane:methanol (1.5 L) containing 1% TEA (300 mL), 9:1 dichloromethane:methanol (1.5 L) containing 2% TEA, 8:2 dichloromethane:methanol (1.5 L) containing 2% TEA (2 L), and 7:3:1 dichloromethane:ethylacetate:methanol with 2% TEA (500 mL). Fractions containing the second major product (blue) to elute from the column were combined and evaporated to give a dark blue solid (4.23 g). This sample was redissolved in water (200 mL), cooled to 0° C. (ice-bath) and acidified with concentrated HCl (~20 mL) to give a dark red precipitate that was filtered and washed with water until the filtrate was neutral. The red solid was dried in air and in vacuo to give 3.13 grams (TLC analysis, 7:3:1 dichloromethane:ethylacetate:methanol+2% TEA) Rf=0.13). $^1$HNMR (d$_6$-DMSO) δ: 8.7 (d, 2H); 8.5 (s, 1H); 8.2 (m, 2H); 7.7 (s, 1H); 7.4 (dd, 2H); 7.3 (dd, 2H); 7.2 (d, 2H); 6.7 (dd, 2H).

5(6)-(2-dimethylaminoethyl)carboxamido)-naphthofluorescein

A sample of 5(6)-carboxynaphthofluorescein (470 mg, 0.95 mmole) was dissolved in dry DMF (10 mL) and O-trifluoroacetyl-N-hydroxysuccinimide (665 mg, 3.15 mmole) and dry pyridine (800 uL, 9.93 mmoles) were added. This solution was allowed to stir at room temperature under anhydrous conditions for 18 hours. The reaction mixture was then diluted with ethylacetate (100 mL) and extracted with ice-water (2×100 mL), 1 N HCl (1×100 mL) and brine solution (1×100 mL). The combined aqueous layers were back-extracted with ethylacetate (25 mL) and the combined organic layers were dried over anhydrous sodium sulfate, filtered and evaporated in vacuo to give a blue solid (180 mg, 32%). TLC analysis (irrigant=9:1 dichloromethane:methanol; Rf=0.30). A sample of the NHS esters (150 mg, 0.262 mmole) was dissolved in anhydrous DMF (10 mL) and unsym-dimethylethylenediamine (50 uL, 453 mmole) was added. This solution was allowed to stir under dry N$_{2(g)}$ at room temperature overnight. The reaction was evaporated and dried in vacuo overnight to a tan oil, that was resuspended in acetonitrile (5 mL) and water (10 mL). The solution was acidified with 1 N HCl until the color changed from yellow to red. The sample was evaporated and co-evaporated with acetonitrile (2×20 mL), and crystallized from cold acetonitrile (10 mL) to give a purple solid (43 mg, 29%) TLC analysis (irrigant=5:5:3:1 pyridine:ethylacetate:acetic acid:water) Rf=0.42). $^1$H-NMR (d$_6$-DMSO) exhibited two isomers in approx. 2:1 ratio.

5(6)-(2-dimethylaminoethyl)carboxamido)-naphthofluorescein diacetate

A sample of 5(6)-(2-dimethylaminoethyl)carboxamido)-2'7'-dichlorofluorescein (21 mg, 35 umole) was suspended in dry dichloromethane (2 mL), cooled to 0° C. (ice-bath) under dry N$_{2(g)}$ and acetic anhydride (0.5 mL, 5.3 mmole) and dry pyridine (0.5 mL, 6.2 mmole) were added. This reaction mixture was allowed to stir under anhydrous conditions at 0° C. for 2 hours and at room temperature overnight. The resulting clear, pale orange solution was treated with ice-cold water (2 mL), and extracted. The resulting organic layer was washed with ice-cold saturated sodium bicarbonate solution (3 mL), 0.1 N citric acid solution (2 mL) and water (2 mL). The resulting organic layer was dried over anhydrous sodium sulfate, filtered, evaporated and dried in vacuo to give a light tan sample (16 mg) that was recrystallized from methanol:water (1:1, 10 mL). The resulting light salmon colored powder was dried in vacuo (yield=14 mg, 64%).

Example 11

Preparation of a Benzoxazolylcoumarin Esterase Substrate with Blue Fluorescence after Enzyme Activity The following compound was prepared:

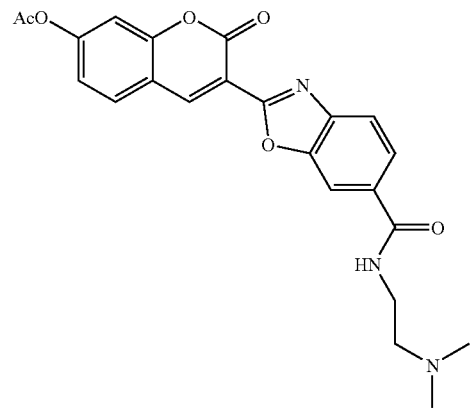

M1322

2-Cyanoacetimide, Ethyl ester, hydrochloride

A solution of diethylether (30 mL) and absolute ethanol (9.01 mL, 154.4 mmole) was cooled to 0° C. (ice-bath) and acetyl chloride (5.49 mL, 77.20 mmole) added slowly with stirring. This solution was allowed to react for 30 minutes, and added to a solution of malononitrile (5.10 grams, 77.20 mmole) in anhydrous diethylether (20 mL). The above mixture was allowed to react at 0° C. overnight. The abundant white precipitate was filtered, dried in air and in vacuo to give a light yellow crystalline product after drying (7.88 g, 69%). TLC analysis (7:3 ethylacetate:methanol) showed a single product Rf=0.77).

4-Amino-3-hydroxybenzoic acid, ethyl ester, hydrochloride salt

To a dry 100 mL round-bottom flask was added absolute ethanol (50 mL) and the solution cooled to 0° C. (ice-bath) under dry N$_{2(g)}$. Acetyl chloride (5.0 mL) was added slowly with stirring and this solution allowed to stir under anhydrous conditions for 2 hours to prepare anhydrous 1.40 M HCl in ethanol. To this solution was added 4-amino-3-hydroxybenzoic acid (2.50 g, 16.32 mmole) and the mixture allowed to stir as above at room temperature overnight. TLC (irrigant=7:1:1:1 ethylacetate:methanol:water:acetic acid, Rf=0.85) indicated complete conversion to the ethyl ester. Yield 3.5 g (99%).

5-Carboxyethyl-2-cyanomethylbenzoxazole

A solution of 2-cyanoacetimide, ethyl ester, hydrochloride (1.49 g, 10 mmole) and 4-amino-3-hydroxybenzoic acid, ethyl ester, hydrochloride salt (2.17 g, 10 mmole) in anhydrous dichloromethane (25 mL) was heated to gently reflux overnight, cooled to room temperature, diluted with dichloromethane (100 mL) and extracted successively with water, 1 N HCl, saturated sodium bicarbonate solution and water (1×100 mL each). The resulting organic layer was dried over anhydrous sodium sulfate, filtered, evaporated and dried in vacuo to give an oil (0.98 g, 43%) that was used without further purification. TLC analysis (9:1 dichloromethane:methanol) Rf=0.88).

3-(3'-Carboxyethylbenzoxazolyl)-7-hydroxycoumarin

5-Carboxyethyl-2-cyanomethylbenzoxazole (0.98 g, 4.26 mmole) was dissolved in absolute ethanol (20 mL) and 2,4-dihydroxybenzaldehyde (589 mg, 4.26 mmole) and ammonium acetate (406 mg) added. The solution was allowed to stir under anhydrous conditions overnight. The reaction was cooled to −18° C., and the abundant yellow-orange precipitate was filtered and washed with minimum ice-cold absolute ethanol, dried in air and in vacuo to give the title compound (900 mg, 60%) as a bright yellow solid. TLC analysis (irrigant=9:1 dichloromethane:methanol) Rf=0.65. A second crop (240 mg) was obtained from the filtrate with concentration and cooling, but was the free acid (TLC irrigant=9:1:1 dichloromethane:methanol:acetic acid, Rf=0.25).

3-(3'-[Carboxamidoethyl-2-dimelhylamino]lbenzoxazolyl)-7-hydroxycoumarin

A sample of 3-(3'-Carboxyethylbenzoxazolyl)-7-hydroxycoumarin (400 mg, 1.14 mmole) was suspended in unsym-dimethylethylenediamine (4.0 mL, 36.3 mmole), the vial capped and allowed to stir at room temperature for 72 hours. The reaction mixture was poured into diethylether (200 mL) to crystallize, and after drying gave the title compound as a tan powder (72 mg, 16%). TLC analysis (irrigant=9:1:1 dichloromethane:methanol:acetic acid) Rf=0.02.

3-(3'4-[Carboxamidoethyl-2-dimethylamino]lbenzoxazolyl)-7-acetoxycoumarin

A sample of 3-(3'-[Carboxamidoethyl-2-dimethylamino]lbenzoxazolyl)-7-hydroxycoumarin (72 mg, 0.183 mmoles) was suspended in dry dichloromethane (2 mL) using ultrasonication, and acetic anhydride (1.0 mL, 10.6 mmole) and dry pyridine (1.0 mL, 12.4 mmole) added. This mixture was allowed to stir overnight, and the resulting product solution, diluted with dichloromethane (30 mL) and extracted with water (1×50 mL), saturated sodium bicarbonate solution (1×50 mL), 1 N HCl (1×50 mL) and water (1×50 mL). The resulting dichloromethane layer was dried over anhydrous sodium sulfate, filtered and evaporated. Drying in vacuo provided an off-white solid (66 mg, 83%). A biocompatible solution of this substrate was prepared by dissolving 44 mg in dry DMSO (1.0 mL) for staining live cells for esterase activity.

Example 12

Preparation of a Hexosaminidase Substrate with Red Fluorescence after Enzyme Activity The following compound was prepared:

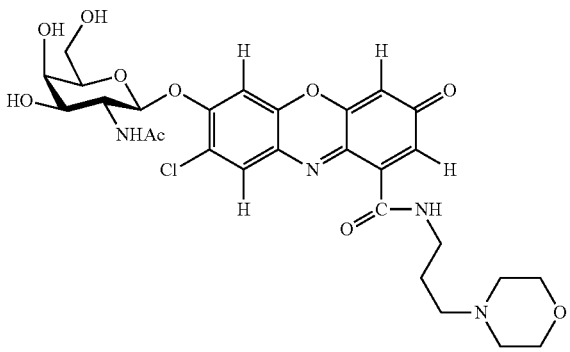

4-Chloro-2-nitrosoresorcinol

A solution of anhydrous ethanol (100 mL) under dry nitrogen gas was cooled in an ice-bath (0° C.) and solid sodium metal (2.3 g, 100 mmole) added with stirring until dissolved. 4-chlororesorcinol (14.4 g, 100 mmole) was added with stirring until dissolved (20 min.) and a solution of N-butylnitrite (10.3 g, 100 mmole) in absolute ethanol (10 mL) added dropwise with stirring. This solution was allowed to react for 3 hours at (0° C.), and then poured into ice-water (300 mL) and acidified with 1 N aqueous HCL solution (~100 mL) until the pH was 2-3. The resulting solid was collected by filtration, washed with water and dried in vacuo to give a solid (6.4 g, 37%). TLC analysis showed a single spot (irrigant=5:1 ethylacetate:methanol) Rf—0.40.

3-Chloro-5-carboxyresurufin

4-Chloro-2-nitrosoresorcinol (6.10 g, 35.1 mmole) and 3,5-dihydroxybenzoic acid (5.41 g, 3.51 mmole) was suspended in anhydrous methanol (140 mL) and cooled to −5° C. in an ice-methanol bath. Solid manganese dioxide (3.40 g) was added followed by conc. sulfuric acid (3.7 mL) dropwise keeping the temperature between 0° and 5° C. The ice-methanol bath was removed and the dark red mixture allowed to stir at room temperature for 2 hours. The solution was then filtered through a fluted filter paper, and conc. ammonium hydroxide added until the filtrate changed to a dark green-blue color. This solution was again filtered through a Celite™ 545 pad and additional ammonium hydroxide added (20 mL). This basic solution was cooled in an ice-bath with stirring and the pH was adjusted to 2 with aqueous HCl solution. The resulting solution was evaporated to dryness and redissolved in methanol (30 mL) and applied to silicagel 60, with evaporation. The solid sample was applied to a column of silicagel 60 (70-230 mesh, 45×2 cm) and eluted by gradient elution with 20%, 25% and 30% methanol in dichloromethane (1 L each) and 40% methanol in dichloromethane (500 mL). The third set of fractions contained the title dye (2.70 g, 26%). TLC (irrigant=1:1 dichloromethane:methanol, Rf=0.58).

3-Chloro-5-carboxyresorufin, ethyl ester

To a dry flask under dry nitrogen gas was added absolute ethanol (50 mL) and cooled to in an ice-bath. Acetyl chloride (3.56 mL, to make 1 M HCl/EtOH) was added and this solution allowed to stir at 0° C. for 15 min. A sample of 3-Chloro-5-carboxyresorufin (303 mg, 1.04 mmole) was added and the solution allowed to stir under anhydrous conditions at room temperature overnight. The solvents were evaporated at reduced pressure (rotovap) and co-evaporated with abs. ethanol (2×10 mL) and dried in vacuo to give a dark red solid (0.36 grams) that was purified by column chromatography (silicagel 60, 70-230 mesh column 25×400 mm, elution with 20:1 dichloromethane:methanol). Fractions containing the pure ethyl ester were combined and evaporated to give a red solid (41 mg, 12%). TLC analysis (9:1 dichloromethane:methanol) Rf=0.39.

3-Chloro-5-(3-N-morpholinopropyl)carboxamidoresorufin

A sample of 3-Chloro-5-carboxyresorufin, ethyl ester (41 mg, 0.13 mmole) was dissolved in N-(3-aminopropyl)-morpholine (410 uL, 2.8 mmole) and allowed to stir at room temperature for 72 hours. TLC analysis (irrigant=7:3 ethylacetate:methanol) indicated that all of the starting material was consumed and a new product (Rf=0.45) was formed. The reaction mixture was evaporated to dryness and coevaporated with dry methanol. The final oily product was triturated with diethylether to give a red solid (55 mg, 96%).

3-Chloro-5-(3-N-morpholinopropyl)carboxamidoresorufin 2,3,6-tri-O-acetyl-2-deoxy-2-N-Acetyl-β-D-Galactopyranoside A solution of 3-chloro-5-(3-N-morpholinopropyl)carboxamidoresorufin (73 mg, 0.174 mmole), acetobromo-N-acetylgalactosamine (86 mg, 0.20 mmole) and silver carbonate (28 mg, 0.105 mmole) was prepared in anhydrous dichloromethane, and placed under an atmosphere of dry nitrogen gas. 3 A molecular sieves (0.4 g) and 2,4,6-collidine (28 uL, 0.20 mmole) were added and the flask covered in Al-foil (darkness) and allowed to stir under anyhydrous conditions for 3 days. The resulting solution was diluted with dichloromethane (50 mL) and filtered through a Celite™ pad, and the filtrate was extracted with water (50 mL), satd. sodium bicarbonate solution (50 mL), water (50 mL), 1 N aqueous HCl (50 mL), 0.2 N sodium thiosulfate solution (50 mL) and water (50 mL). The final organic layer was dried over anhydrous sodium sulfate, filtered and evaporated to an orange solid (120 mg). TLC analysis exhibited a single major product (irrigant=25:1 dichloromethane; triethylamine) Rf=0.44 contaminated with residual sugar (Rf=0.95) upon sulfuric acid charring. This sample was used for synthesis of the title N-acetylgalactoside.

3-Chloro-5-(3-N-morpholinopropyl)carboxamidoresorufin 2-deoxy-2-N-Acetyl-β-D-Galactopyranoside Under anhydrous conditions, the crude sample of 3-Chloro-5-(3-N-morpholinopropyl)carboxamidoresorufin 2,3,6-tri-O-acetyl-2-deoxy-2-N-Acetyl-b-D-Galactopyranoside (30 mg) was dissolved in anhydrous methanol (20 mL) under an atmosphere of dry nitrogen gas and 25% (w/v) sodium methoxide in methanol (670 uL, 84 mg NaOMe) added with stirring. This solution was allowed to stir under anhydrous conditions for 4 hours, and neutralized with washed, dry IRC50 (H+) resin (about 3 grams) until neutral. The resin was filtered and washed with dry methanol and the combined filtrates were evaporated and dried in vacuo to give an orange glass (20 mg) homogeneous by TLC analysis (irrigant=7:3 ethylacetate:methanol) Rf=0.1. A biocompatible staining solution was prepared by dissolving this sample in dry DMSO and determining the concentration by measuring the absorbance at 457 nm using an extinction coefficient of 17.9K.

Example 13

Preparation of an Alternate Targeting Group with a Long Chain Alkyl Group for Increased Lipophilicity The following compound was prepared:

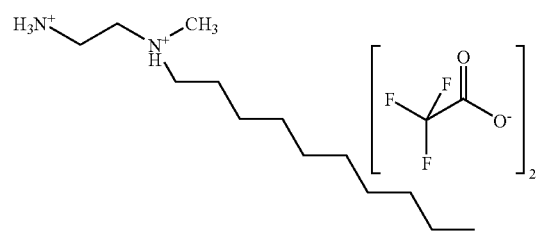

N—BOC—N'-methylethylenediamine

A solution of N-Methylethylenediamine (2.00 g, 27.0 mmol) in DMF/water (1:1, 30 mL) was adjusted to ph 7 with 6 N HCl. A solution of Di-t-butyldicarbonate (5.89 g, 27 mmol) in DMF (20 mL) was added to the stirred solution at room temperature. The pH of the reaction mixture was maintained between 6 and 7 by the periodic addition of 1 N NaOH. The reaction was stirred until the pH remained constant. The reaction was diluted with water (150 mL) and the resulting solution was washed with ethylacetate (3×100 mL). The pH was adjusted to ~11.5 with 10 N NaOH and the resulting solution was extracted with ethylacetate (3×200 mL). The extract was filtered through a cotton plug and the solvent was removed. The resulting liquid was stirred in vacuo overnight at room temperature to yield N—BOC—N'-methylethylenediamine and N—BOC—N-methylethylenediamine as a 1:1 mixture (1.73 g, 41% mass recovery). $^1$H NMR (CDCl$_3$) δ: 1.43 and 1.45 (9H), 1.78 (s, 2H), 2.45 (s, 1.5H), 2.73 (t, 1H), 2.82 (t, 1H), 2.87 (s, 1.5H), 3.27 (m, 2H).

N—BOC—N'-decyl-N'-methylethylenediamine

To a stirred solution of N—BOC—N'-methylethylenediamine and N—BOC—N-methylethylenediamine (1:1, 1.73 g, 4.96 mmol each) in MeOH (50 mL) were added decanal (9.31 g, 59.6 mmol) followed by sodium cyanoborohydride (585 mg, 9.31 mmol) at room temperature. The reaction was stirred overnight at room temperature. The reaction was concentrated on a rotevaporator and the concentrate was diluted with water (50 mL). The pH was lowered to ~2 with 6 N HCl and the acidic solution was extracted with ethylacetate (3×100 mL). The amine products were extracted into the organic phase. The ethylacetate portion was washed with 0.1 N NaOH (1×100 mL) and brine (2×100 mL) and the solvent was removed. The resulting liquid was dried overnight in vacuo at room temperature. The product was isolated by column chromatography on silica gel column (4×15 cm). Side products were eluted from the column with 1 and 2% MeOH in CH$_2$Cl$_2$ then the product was eluted with 5 and 10% MeOH in CH$_2$Cl$_2$. The solvent was removed from the product fractions and the residue was dried in vacuo at rt to yield N—BOC—N'-decyl-N'-methylethylenediamine as a pale yellow solid (470 mg, 21%): TLC (silica gel, 1 MeOH:9 CH$_2$Cl$_2$) R$_f$=0.6; $^1$H NMR (DMSO-d$_6$) δ 0.82 (t, 3H), 1.23 (s, 16H), 1.35 (s, 9H), 2.10 (s, 3H), 2.25 (m, 4H), 2.95 (m, 2H), 6.80 (s, 1H).

N-decyl-N-methylethylenediamine-bis-trifluoroacetic acid salt

A solution of N—BOC—N'-decyl-N'-methylethylenediamine (450 mg, 1.43 mmol) in TFA (15 mL) was allowed to stand at room temperature for 30 min. The TFA was removed on a rotevaporator and the resulting oil was dried in vacuo for 1 h to give a semi-solid. The semi-solid was triturated with ether (15 mL) and the resulting suspension was stored overnight in a freezer. The resulting solid was collect by vacuum filtration and was washed repeatedly with ether. The filter cake was dried in vacuo to yield N-decyl-N-methylethylenediamine-bis-trifluoroacetic acid salt as a colorless crystalline solid (470 mg, 74%): $^1$H NMR (DMSO-d$_6$) δ 1.80 (t, 3H), 1.22 (s, 16H), 1.58 (m, 2H), 2.80 (s, 3H), 3.08 (m, 2H), 3.25 (m, 2H), 8.22 (bs, 3H).

Example 14

Preparation of an Alternate Targeting Group with Two Long Chain Alkyl Groups for Increased Lipophilicity The following compound was prepared:

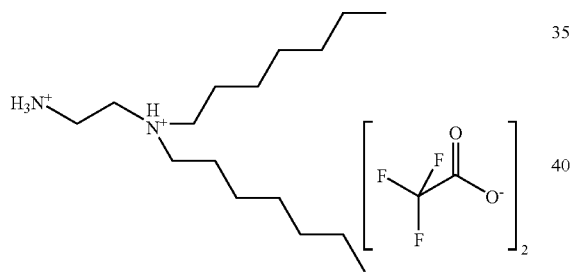

N—BOC—N',N'-Diheptylethylenediamine

To a stirred solution of N—BOC-ethylenediamine (500 mg, 3.12 mmol) in MeOH (15 mL) were added heptanal (802 mg, 7.02 mmol) followed by sodium cyanoborohydride (588 mg, 9.36 mmol) and the reaction was stirred overnight at room temperature. The reaction was concentrated on a rotevaporator and the concentrate was diluted with water (50 mL). The pH was lowered to ~2 with 6 N HCl and the acidic solution was extracted with ethylacetate (3×100 mL). The layer was washed with 0.1 N NaOH (1×100 mL) and brine (2×100 mL) and the solvent was removed. The product was isolated by column chromatography on silica gel. The solvent was removed from the product fractions and the residue was dried in vacuo at room temperature to yield two major products N—BOC—N',N'-diheptylethylenediamine (0.51 g, 46%): TLC (silica gel, 1 MeOH:9 CH$_2$Cl$_2$) R$_f$=0.81; and N—BOC—N'-heptylethylenediamine (0.23 g, 15%): TLC (silicagel 9:1 dichloromethane:methanol) Rf=0.66.

N,N-Diheptylethylenediamine-bis-trifluoroacetic acid salt

A solution of N—BOC—N',N'-diheptylethylenediamine (x mg, x mmol) in TFA (x mL) was allowed to stand at room temperature for 30 min. The TFA was removed on a rotevaporator and the residue was dried in vacuo for 1 h at room temperature. The residue was triturated with ether (x mL) and the resulting suspension was stored overnight in a freezer. The resulting solid was collect by vacuum filtration and was washed repeatedly with ether. The filter cake was dried in vacuo at room temperature to yield N,N-diheptylethylenediamine, bis-trifluoroacetic acid salt as a solid (613 mg, 90%). Deblocking of the mono-heptyl targeting group was performed in a similar manner to yield the N-heptylethylenediamine, bis-trifluoroacetic acid salt.

Example 15

Preparation of an Esterase Substrate with Blue Fluorescence after Enzyme Activity and Containing an Increased Lipophilic Targeting Group The following compound was prepared:

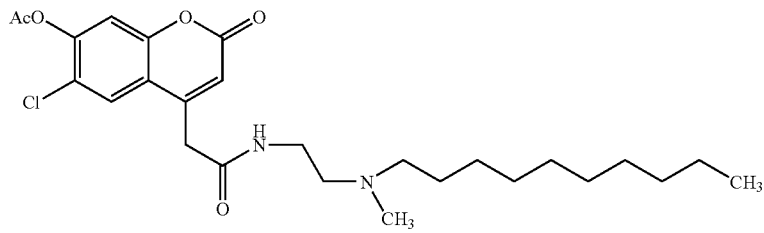 [SMILES: CCCCCCCCCCN(C)CCNC(=O)Cc1cc(=O)oc2cc(OC(C)=O)c(Cl)cc12]

2-(6-Chloro-7-hydroxycoumarin 4-yl)-N-[2-(N-decyl-N-methyl-amino)ethyl]acetamide A solution of 1 N KOH (7.34 mL) was added to a suspension of Ethyl 6-Chloro-7-hydroxycoumarin-4-carboxylic acid (1.00 g, 3.54 mmol) in ethanol (75 mL) with stirring at room temperature to give a yellow to brown solution. The ethanol portion was concentrated. The concentrate and the oily residue were dissolved in H$_2$O (50 mL) and the pH of the resulting solution was adjusted to ~6 to 7 with 1 N HCl. The solution was washed with ethylacetate (3×100 mL) to removed any residual ethyl ester. The pH was lowered to ~2 with 1 N HCl and the acidic solution was extracted with ethylacetate (3×100 mL). The extract was washed with saturated brine (2×100 mL) and was dried over Na$_2$SO$_4$. Solvent removal gave the carboxylic acid as a beige solid (670 mg, 75%): TLC (silica gel 1:3 MeOH:EtOAc) R$_f$=0.2. Without purification the above acid (670 mg, 2.63 mmol) was dissolved in DMF (25 mL) and the resulting solution was added to solid N-hydroxysuccinimide trifluoroacetate (3.74 g, 17.7 mmol). Pyridine (5 mL) was added to the resulting solution and the reaction was stirrer overnight at room temperature. The reaction was poured onto ice and diluted with H$_2$O (250 mL). The pH was lowered to 2 with 1 N HCl and the solution was extracted with ethylacetate (2×100 mL). The extract was washed with saturated brine (2×100 mL) and was dried over Na$_2$SO$_4$. The solvent was removed and the gummy residue was washed with a small amount of ethylacetate. The resulting solid was collected by vacuum filtration and was dried in vacuo to yield the N-hydroxy-succinimidyl ester as a beige solid (750 mg, 81%): TLC (silica gel 1:9 MeOH:CH$_2$Cl$_2$) R$_f$=0.8. A portion of the above N-hydroxysuccinimidyl ester (280 mg, 0.796 mmol) was combined with N-decyl-N-methylethylenediamine-bis-trifluoroacetic acid salt (282 mg, 0.637 mmol) and Ethyl diisopropyl amine (169 mg, 1.31 mmol) in DMF (1 mL). The resulting solution was stirred overnight at room temperature. Trifluoroacetic acid (114 mg, 1.00 mmol) was added to the reaction. The volatile portion was removed in vacuo at 50° C. to give a gummy solid. The solid was triturated with ethylacetate (1 to 2 mL) to give a suspension. The solid was collected by vacuum filtration and was washed with ethylacetate. The filter cake was dried in vacuo to yield 2-(6-Chloro-7-hydroxycoumarin-4-yl)-N-[2-(N-decyl-N-methyl-amino)ethyl]acetamide as a colorless solid (148 mg, 51%): TLC (silica gel 1:9 MeOH:CH$_2$Cl$_2$) R$_f$=0.3; $^1$H NMR (DMSO-d$_6$) S:0.81 (t, 3H), 1.22 (s, 16H), 1.58 (m, 2H), 2.60 (s, 3H), 2.80-3.20 (m, 4H), 3.70 (s, 2H), 6.23 (s, 1H), 6.90 (s, 1H), 7.78 (s, 1H), 8.43 (t, 1H).

2-(6-Chloro-7-acetoxycoumarin-4-yl)-N-[2-(N-decyl-N-methyl-amino)ethyl]acetamide A sample of this 2-(6-Chloro-7-hydroxycoumarin-4-yl)-N-[2-(N-decyl-N-methyl-amino)ethyl]acetamide (26 mg, 0.06 mmole) was dissolved in anhydrous dichloromethane (5 mL) and acetic anhydride (0.5 mL, 5.3 mmole) and dry pyridine (0.5 mL, 6.2 mmole) added. This mixture was allowed to stir overnight, and the resulting solution, diluted with dichloromethane (30 mL) and extracted with water (1×25 mL), saturated sodium bicarbonate solution (1×25 mL), 1N HCl (1×25 mL) and water (1×25 mL). The resulting dichloromethane layer was dried over anhydrous sodium sulfate, filtered and evaporated. Drying in vacuo provided an off-white solid (22 mg, 79%). A biocompatible solution of this substrate was prepared by dissolving 22 mg in dry DMSO (0.446 mL) for staining live cells for esterase activity.

Example 16

Preparation of a β-Glucosidase Substrate with Blue Fluorescence after Enzyme Activity and an Increased Lipophilic Targeting Group The following compound is prepared:

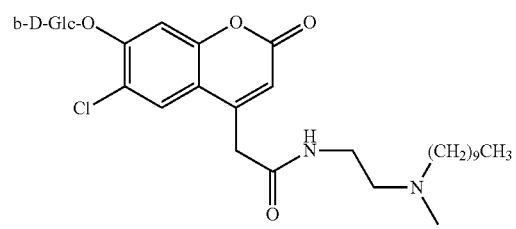

A sample of 2-(6-Chloro-7-hydroxycoumarin-4-yl)-N-[2-(N-decyl-N-methyl-amino)ethyl]acetamide (50 mg, 0.11 mmole) was dried in vacuo overnight, placed under anhydrous N2(g), and acetobromoglucose (77 mg, 0.28 mmole, 2.5 equiv.) added. These solids were suspended in anhydrous dichloromethane (15 mL) and solid, dry silver carbonate (39 mg, 0.14 mmole), sym-collidine (37 uL, 0.28 mmole), dry 3 A molecular sieves (0.5 g) were added. This reaction mixture was covered in Al-foil (darkness) and allowed to stir under anhydrous conditions for 3 days. After this time, the reaction mixture was filtered through a bed of diatomaceous earth (Celite™ 545) and the precipitate washed with excess dichloromethane. The combined filtrates were washed with water, saturated aqueous sodium bicarbonate solution, 1 N HCl, 0.2 N sodium thiosulfate solution and water (each 1×50 mL). The organic layer was dried over anhydrous sodium sulfate, filtered, evaporated to a low volume and applied to a slurry-packed column of silicagel 60 (70-230 mesh, 50 g, 40×60 mm) prepared in dichloromethane. The product was eluted by gradient elution, using dichloromethane (500 mL), 8:2 dichlorormethane:ethylacetate (500 mL), 6:4 dichloromethane:ethylacetate (500 mL) and 9:1 dichloromethane: methanol (500 mL). Fractions containing the first major quenching (UV 254 nm) product to elute from the column were combined, evaporated and dried in vacuo to give a clear oil (70 mg). TLC (8:2 dichloromethane:ethylacetate, Rf=0.75).

This peracetate was dried in vacuo overnight, placed under anhydrous N$_{2(g)}$ and dissolved in anhydrous methanol (40 mL). To this solution was added 25% (w/v) sodium methoxide in methanol (90 mg, 1.66 mmole) and this mixture allowed to stir under anhydrous conditions for 2.5 hours. The reaction mixture was then neutralized with washed, dry IRC-50 (H+) resin, allowing the resin to stir for about 30 min. The resin was filtered and washed with excess dry methanol, evaporated to a low volume (about 5 mL) (rotary evaporator, T<35° C.) and crystallized by adding dry diethylether (100 mL). The solution was stored at 4° C. overnight to complete crystallization, and the off-white crystals filtered and washed with fresh diethylether to give an off-white crystalline solid (41 mg, 55%). TLC analysis (irrigant=9:1:1 dichloromethane:methanol:acetic acid, Rf=0.22). Biocompatible solutions of the product were prepared in DMSO for cell staining experiments.

Example 17

Preparation of a β-Galactosidase Substrate with Blue Fluorescence after Enzyme Activity and an Increased Lipophilic Targeting Group The following compound is prepared:

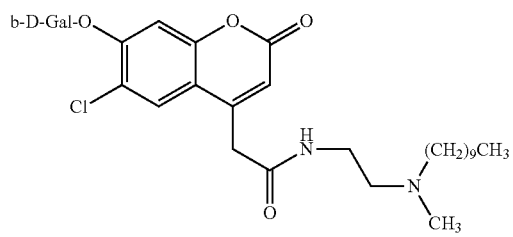

A sample of 2-(6-Chloro-7-hydroxycoumarin-4-yl)-N-[2-(N-decyl-N-methyl-amino)ethyl]acetamide (50 mg, 0.11 mmole) was dried in vacuo overnight, placed under anhydrous N2(g), and acetobromogalactose (77 mg, 0.28 mmole, 2.5 equiv.) added. These solids were suspended in anhydrous dichloromethane (15 mL) and solid, dry silver carbonate (39 mg, 0.14 mmole), sym-collidine (37 uL, 0.28 mmole), dry 3 Å molecular sieves (0.5 g) were added. This reaction mixture was covered in Al-foil (darkness) and allowed to stir under anhydrous conditions for 3 days. After this time, the reaction mixture was filtered through a bed of diatomaceous earth (Celite™ 545) and the precipitate washed with excess dichloromethane. The combined filtrates were washed with water, saturated aqueous sodium bicarbonate solution, 1 N HCl, 0.2 N sodium thiosulfate solution and water (each 1×50 mL). The organic layer was dried over anhydrous sodium sulfate, filtered, evaporated to a low volume and applied to a slurry-packed column of silicagel 60 (70-230 mesh, 50 g, 40×60 mm) prepared in dichloromethane. The product was eluted by gradient elution, using dichloromethane (500 mL), 8:2 dichlorormethane:ethylacetate (500 mL), 6:4 dichloromethane:ethylacetate (500 mL) and 9:1 dichloromethane:methanol (500 mL). Fractions containing the first major quenching (UV 254 nm) product to elute from the column were combined, evaporated and dried in vacuo to give a clear oil (66 mg). TLC (8:2 dichloromethane:ethylacetate, Rf=0.7).

This peracetate was dried in vacuo overnight, placed under anhydrous $N_{2(g)}$ and dissolved in anhydrous methanol (40 mL). To this solution was added 25% (w/v) sodium methoxide in methanol (90 mg, 1.66 mmole) and this mixture allowed to stir under anhydrous conditions for 2.5 hours. The reaction mixture was then neutralized with washed, dry IRC-50 (H+) resin, allowing the resin to stir for about 30 min. The resin was filtered and washed with excess dry methanol, evaporated to a low volume (about 5 mL) (rotary evaporator, T<35° C.) and crystallized by adding dry diethylether (100 mL). The solution was stored at 4° C. overnight to complete crystallization, and the off-white crystals filtered and washed with fresh diethylether to give an off-white crystalline solid (29 mg, 38%). TLC analysis (irrigant=9:1:1 dichloromethane:methanol:acetic acid, Rf=0.20). Biocompatible solutions of the product were prepared in DMSO for cell staining experiments.

Example 18

Preparation of an L-Alanyl Peptidase Substrate with Green Fluorescence after Enzyme Reaction The following compound was prepared:

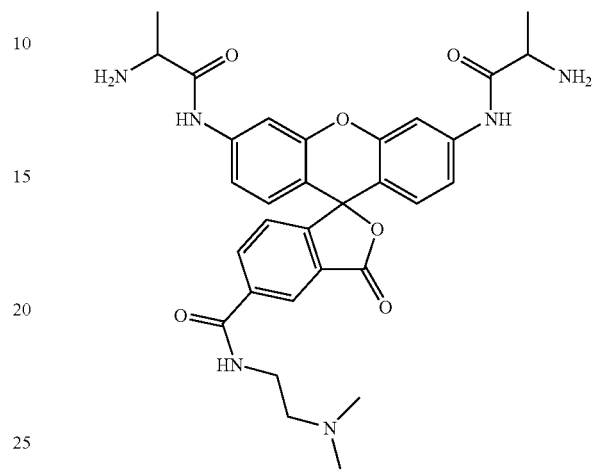

5(6)-Carboxyrhodamine 110

Under anhydrous conditions a mixture of trimellitic anhydride (4.80 g, 25 mmole) and 3-aminophenol (5.46 g, 50 mmole) in anhydrous methanesulfonic acid (15 mL, 231 mmole) was heated to 182° C. for 24 hours with stirring. The reaction was cooled to room temperature and poured into ice-water (200 mL) and allowed to stir for 1 hour to crystallize. The resulting red solid was filtered, and washed with water, dried in air and in vacuo briefly (1 hour) and then digested with 2 N NaOH solution (40 mL). The resulting sodium salt was cooled to 0° C. (added ice-cubes directly to the solution) and concentrated HCl (12 M, 10 mL) was added to acidify (pH 3). The resulting red precipitate was filtered and washed with water until the filtrate was neutral, dried in air and in vacuo to give a red solid 6.72 g (72%), homogeneous by TLC analysis (irrigant=9:1:1 dichloromethane:methanol:acetic acid; Rf=0.02). $^1$H NMR ($d_6$-DMSO) (mixture of 5 and 6 isomers) δ: 8.5 (d, 0.5H); 8.3 (dd, 0.5H); 8.25 (m, 1.5H); 8.2 (br. s, 3H, —NH); 7.9 (s, 0.5H); 7.6 (d, 0.5H); 7.0 (d, 2H); 6.8 (m, 3.5H).

N',N'-di-FMOC-L-Alanyl-5(6)carboxyrhodamine 110

Under anhydrous conditions, N-alpha-(9-fluorenylmethyloxycarbonyl)-L-Alanine (FMOC-L-Ala-OH, 847 mg, 2.72 mmole) was dissolved in anhydrous THF (5 mL) and cooled in a methanol/ice bath (−5° C.). N-methylmorpholine (329 uL, 3.0 mmole) and isobutylchloroformate (392 uL, 3.0 mmole) were added with stirring, and this mixture was allowed to stir for 30 min. at −5° C., and then warmed to room temperature. To this suspension was added a solution of 5(6)-carboxyrhodamine 110 (112 mg, 0.272 mmole) in dry DMF (0.5 mL) containing N-methylmorpholine (33 uL, 0.3 mmole) along with two DMF rinses (1 mL each). This solution was allowed to stir at room temperature overnight with stirring. The reaction mixture was added to water (50 mL) and extracted with ethylacetate (3×25 mL). The resulting combined ethylacetate layers were washed with water (25 mL), saturated sodium carbonate solution (2×25 mL), water (25 mL) and brine solution (25 mL). The final ethylacetate layer was dried over anhydrous sodium sulfate, filtered and dried to an orange foam that was redissolved in dichloromethane (3 mL) and purified on a column of silicagel 60 (70-230 mesh, 19×2.5 cm) slurry packed in 3:1 hexanes:ethylacetate. The product was eluted by gradient elution using 25% ethylacetate:hexanes (300 mL), 30% ethylacetate:hexanes (400 mL) and 40% ethylacetate:hexanes (600 mL). Fractions containing the product were combined and evaporated and dried in vacuo to give a colorless solid (211 mg). $^1$H NMR (CDCl$_3$) was consistent with the title structure, with some extra peaks from some excess free amino acid. This product was used for the synthesis of the amide.

N,N'-di-L-Alanyl-5(6)-(2-dimethylaminoethyl)carboxamido)-rhodamine 110

The crude sample of N,N'-di-FMOC-L-Alanyl-5(6)carboxyrhodamine 110 (211 mg, 0.205 mmole) was dissolved in dry DMF under anhydrous N$_{2(g)}$ and ethyl 3-(dimethylamino) propyl carbodiimide (43 mg, 0.225 mmole, 1.1 equiv.) and N-hydroxysuccinimide (NHS, 76 mg, 0.225 mmole, 1.1 equivalents) added. This solution was allowed to stir at room temperature for 5 hours, and unsym-dimethylethylenediamine (225 uL, 2.0 mmole, 10 equiv.) was added and the reaction continued stirring for 18 hours. After this time, ethylacetate (25 mL) and water (25 mL) were added, the layers were separated, and the ethylacetate layer was washed with water (25 mL), saturated sodium bicarbonate solution (25 mL) and water (25 mL). The organic layer was dried over anhydrous sodium sulfate, filtered, and the solvent removed by vacuum distillation (rotovap). The resulting NHS ester was purified by preparative TLC (20×20 cm, 1 mm thickness), using 30% ethylacetate:dichloromethane as eluent, to give an off-white solid (168 mg), showing two main products by TLC analysis (irrigant=3:1 dichloromethane:methanol). The sample was redissolved in dry DMF (5 mL) and piperidine (200 uL, 2.0 mmole) added. After stirring for 6 hours at room temperature, the solution was dried in vacuo and triturated with diethylether (2×25 mL) to give a white powder (111 mg, 92%).

Example 19

Preparation of Cells in Culture for Labeling

Human skin fibroblasts from Lysosomal Storage Disease patients (Krabbe, Tay-Sachs, Sandhoff, Wolman, and Gaucher diseases) were obtained from the Istituto Giannina Gaslini (Genova, Italy). Cell lines were maintained in RPMI 1640 Medium (HyClone) supplemented with 9% Fetal Bovine Serum (Gibco) and 1× Antibiotic/Antimycotic (Gibco). Cells were grown to 90% confluence and passaged by splitting at a 1:5 ratio. Cells were incubated at 37° C., with 5% CO$_2$ atmosphere.

Human skin fibroblasts from a healthy specimen were obtained from the Coriell Institute for Medical Research (Camden, N.J.). Cells were maintained in Minimum Essential Medium Eagle (EMEM) (Lonza) supplemented with 9% Fetal Bovine Serum (Gibco) and 1× Antibiotic/Antimycotic (Gibco). Cells were grown to 90% confluence and passaged by splitting at a 1:5 ratio. Cells were incubated at 37° C., with 5% CO$_2$ atmosphere.

NIH 3T3 and CRE BAG 2 (murine tumor fibroblast) cell lines were obtained from the American Type Culture Collection (Manassas, Va.). Cells were maintained in Dulbecco's Modified Eagles Medium (DMEM) (Sigma) supplemented with 9% Fetal Bovine Serum (Gibco) and 1× Antibiotic/Antimycotic (Gibco). Cells were grown to 70% confluence and passaged by splitting at a 1:10 ratio. Cells were incubated at 37° C., with 5% CO$_2$ atmosphere.

Example 20

Preparation of Labeling Solutions for Mammalian Cell Systems

The desired substrate of the invention is separately dissolved in DMSO to prepare a 10 mM stock solution. The stock solution is kept sealed in small aliquots, at −20.degree. C. The stock solution is kept frozen at all times until use, and exposure to light is minimized. One aliquot of dye stock is taken from the freezer immediately before an experiment and thawed completely at room temperature. The labeling solution is then prepared by adding the dye stock solution to fresh serum-free culture medium (37.degree. C.) in an amount sufficient to make final dye concentrations ranging from 1-200 µM. Dye stock solutions are added such that the final concentration of DMSO in the labeling solution does not exceed 2%.

Example 21

Labeling of Lysosomes and Acidic Organelles in Live Animal Cells

Cells prepared according to Example 19 are transferred to the labeling solution containing either M1268, M1299, M1322, or M1344, and incubated at 37.degree. C. for 15 to 150 minutes. The cells are then washed with pre-warmed fresh medium that does not contain serum (37° C.) and observed using a fluorescence microscope equipped with appropriate filters, such as an XF68 filter set (Omega Optical).

Example 22

Staining of Lysosomes and Chromatin in Living Cells Using an Additional Detection Reagent Cells prepared according to Example 19 are transferred to the labeling solution containing 10 µM M1344 and 2 µg/mL of the nuclear stain DAPI and incubated at 37° C. for 90 minutes. The cells are then washed with fresh, pre-warmed culture medium that does not contain serum and examined under a fluorescence microscope equipped with multiband-pass filter set, such as an XF68 filter set (Omega Optical). As both dyes are organelle-specific, the lysosomes and other acidic organelles stain are stained a bright fluorescent green, while the nuclei are simultaneously stained fluorescent blue.

Example 23

Differential Staining with for Lipase Activity with Lipase Inhibition

Cells were cultured as described in Example 19. Medium was removed from healthy exponentially growing human skin fibroblasts and cells were washed with Phosphate Buffered Saline to remove residual Fetal Bovine Serum. Tetrahydrolipostatin (THL) inhibitor solution was prepared by diluting 10 mM stock solution (in 6:4 DMSO:EtOH) to 200 µM in unsupplemented EMEM. Control solution was prepared by addition of 6:4 DMSO:EtOH at equal concentration as in inhibitor solution. Cells were incubated in either control or inhibitor solution for 3 hours at 37° C., 5% $CO_2$ atmosphere.

Control or inhibitor solutions were removed and cells were washed with Phosphate Buffered Saline. Substrate solution was prepared by diluting 5 mM stock solution (in DMSO) to 10 μM in unsupplemented EMEM. Cells were incubated in substrate solution for 1.5 hours at 37° C., 5% $CO_2$ atmosphere. Substrate solution was then removed, and cells washed 3 times with Phosphate Buffered Saline. Cells were imaged using an XF68 filter set (Omega Optical). Four images of each treatment were processed using cell profiler imaging software to produce a mean object fluorescence intensity for each group.

The following experimental conditions were used. Cells were incubated in serum-free EMEM containing 200 μM, 750 μM, or 1 mM Tetrahydrolipstatin. Significantly lower staining of lysosomes was observed in inhibited cells versus control cells as shown in Table 12.

TABLE 12

| [THL] | MEAN OBJECT INTENSITY |
| --- | --- |
| 1 MM | 0.113 |
| 750 UM | 0.127 |
| 200 UM | 0.171 |
| UNTREATED | 0.209 |

Example 24

Healthy skin fibroblast cells GM03440 were seeded into a 6-well tissue culture plate (FALCON 353046) and cultured in Minimum Essential Medium Eagle (EMEM) supplemented with 9% Fetal Bovine Serum (Gibco) and 1× Antibiotic/Antimycotic solution (Gibco). Cells were allowed to adhere to the plate surface. Cells were incubated for 48 hours, 37° C., 5% $CO_2$ humidification. Medium was removed, and cells washed with Phosphate Buffered Saline to remove residual serum and treatment compounds. Cells were incubated in serum-free EMEM containing 20 μM M1322 for 1.5 hours. Medium was removed, and cells were then washed three times with Phosphate Buffered Saline and mounted in the same. Cells were imaged using an XF06 (DAPI) filter set (Omega Optical). Nine images of each treatment (Chloroquine, Retinoic Acid, Colchicine, Untreated) were processed using Cell Profiler imaging software to produce a mean object fluorescence intensity for each group.

The following experimental conditions were used. Chloroquine (10 mM DMSO stock) was added to a final concentration of 10 μM. Retinoic Acid (10 mM EtOH stock) was added to a final concentration of 10 μM. Colchicine (1 mM stock in sterile Phosphate Buffered Saline) was added to a final concentration of 1 μM. One set of wells was left untreated. The results, shown in Table 2, indicate that the effect of drug administration on esterase enzyme activity in these cell lines could be monitored using the substrate M1322 in a live cell format.

TABLE 2

| TREATMENT | MEAN OBJECT INTENSITY | PUBLISHED EFFECT ON LYSOSOMES |
| --- | --- | --- |
| UNTREATED | 0.136 | N/A |
| RETINOIC ACID | 0.149 | INDUCER |
| COLCHICINE | 0.181 | INCREASES PH |

TABLE 2-continued

| TREATMENT | MEAN OBJECT INTENSITY | PUBLISHED EFFECT ON LYSOSOMES |
| --- | --- | --- |
| CHLOROQUINE | 0.161 | INCREASED STORAGE OF POLAR LIPIDS. |

Example 25

Staining of Mammalian Cells for Aryl Sulfatase Activity

Cells were cultured as described in Example 19. Medium was removed from healthy exponentially growing human skin fibroblasts and cells were washed with Phosphate Buffered Saline to remove residual Fetal Bovine Serum. Substrate solution was prepared by diluting 10 mM stock solution (in DMSO) to 200 μM in unsupplemented EMEM. Cells were incubated in substrate solution for 1.5 hours at 37° C., 5% $CO_2$ atmosphere. Substrate solution was then removed, and cells washed 3 times with Phosphate Buffered Saline. Cells were imaged using a B-2A filter set (Nikon).

Imaged cells showed punctate fluorescent green staining. Very little cytosolic staining of the cells was observed.

Example 26

Detection of an Additional Detection Reagent in Lysosomes

GM03440 cells are incubated for 30 minutes in a solution of culture medium and 100 μg/mL *Datura stramonium* (jimson weed) lectin conjugated to fluorescein at 37° C. in a tissue culture incubator. This green fluorescent lectin has been shown to be taken up by live cells and trafficked to lysosomes. The cells are rinsed twice in fresh culture medium at 37° C., and then are allowed to recover in culture medium without lectin for 4 hours at 37° C. Following recovery, the cells are incubated with 20 μM M1322 and diluted in growth medium for 30 minutes at 37° C. The cells are then rinsed in growth medium without substrate and mounted in the same.

Observation of the stained sample reveals blue and blue-green structures within the cells. The observed blue-green fluorescence indicates colocalization of the green fluorescent lectin conjugate with the blue emission of the substrate turnover in lysosomes. The blue structures indicate the staining of acidic organelles that are not lysosomes.

Example 27

The Effect of $NH_3$ Alkalization on Acidic Organelle Staining in Live Cells

Cell samples prepared according to Example 19 are transferred to two tissue culture dishes. The cells in the first dish are pre-incubated with 1 mM $NH_4OH$ for 30 minutes at 37.degree. C. The cells are then washed with fresh medium. The cells in both dishes are then incubated with a labeling solution that is 20 μM M1299 (as described in Example 2) at 37° C. for 30 minutes. The cells are then washed with pre-warmed fresh medium and observed using a fluorescence microscope equipped with an appropriate filter set.

The cells that were not initially alkalinized display good staining, with all of the lysosomes and other acidic organelles exhibiting a bright green fluorescence. The initially alkalinized cells, however, show only weak staining of acidic organelles, displaying less than 10% of the fluorescence intensity of the control cells.

Example 28

Triple Labeling of Lysosomes, Golgi Apparatus and Nuclei in Living Cells

A cell sample prepared according to Example 19 are transferred to a tissue culture dish and incubated at 37.degree. C. for 30 minutes in a labeling solution that is 20 μM in M1299 (as described in Example 2), 100 nM in BODIPY TR labeled ceramide (Molecular Probes, Inc., Eugene, Oreg.) and 30 nM in Hoechst 33258 (Molecular Probes, Inc., Eugene, Oreg.). The cells are then washed with fresh, pre-warmed culture medium and examined under a fluorescence microscope equipped with an appropriate filter set, such as Omega XF68. The stained cells display green fluorescent acidic organelles, red fluorescent Golgi apparatus, and blue fluorescent nuclei.

Example 29

Analysis of Cell Viability/Cytotoxicity

A cell sample prepared according to Example 19 is incubated at 37° C. for 30 minutes in a labeling solution that is 20 μM in M1299 and 50 nM in propidium iodide. The stained cells are then washed with fresh, pre-warmed culture medium. The cells are examined under a fluorescence microscope equipped with an appropriate filter set. Dead cells exhibit fluorescent red nuclei, while live cells exhibit green fluorescent acidic organelles. Cells that have damaged (i.e. permeant) cell membranes, yet retain an acidic pH gradient with their acidic organelles will display both green and red fluorescence.

What is claimed is:

1. A method of detecting native enzyme activity in acidic organelles, comprising:
  a) combining a sample that comprises mammalian cells with a solution comprising a substrate of the formula:

$T$-LINK-$F(R)$-BLOCK($R'$)

wherein
  T represents a targeting group that is a weakly basic amine containing moiety that partitions the substrate to the acidic organelle;
  F represents a reporter moiety comprising one or more substituents R independently selected from the group consisting of hydrogen, halogen, alkyl, alkenyl, aryl, and heteroaryl;
  BLOCK is a monovalent moiety adapted to be cleaved from the remainder of the substrate by action of a specific enzyme native to said acidic organelle, resulting in a visible signal at the site of enzyme reaction;
  R' is selected from the group consisting of an unsubstituted carboxylic acid
  ester and an alkyoxy substituted carboxylic acid ester;
  LINK has the formula $-(CH2)_a(CONH(CH2)_b)_z$, where a is an integer from 0-5, b is 1-5 and z is 1; and
  b) detecting the presence of a visible signal, wherein said sample is combined with said substrate in a concentration greater than 10 μM and less than 2 mM for a time sufficient for said native enzyme to remove BLOCK and produce said visible signal.

2. The method of claim 1, wherein said acidic organelle is selected from the group consisting of an endosome and a lysosome.

3. The method of claim 1, wherein said visible signal is selected from the group consisting of fluorescence, chemiluminescence and chromogenic staining.

4. The method of claim 1, wherein said BLOCK is selected from the group consisting of: (i) a monovalent moiety derived by removal of a hydroxy group from phosphate or sulfate, (ii) a biologically compatible salt of (i); (iii) a monovalent moiety derived by removal of a hydroxy group from a carboxy group of an aliphatic, aromatic or amino acid or of a peptide; and (iv) a monovalent moiety derived by removal of an anomeric hydroxy group from a mono- or polysaccharide.

5. The method of claim 1, wherein said, wherein F is selected from the group consisting of an anthracene, a benzphenalenone, a coumarin, a fluorescein, a naphthofluorescein, a naphthalene, a phenalenone, a pyrene, a resorufin, a dioxetane, an indole, a luminol and a rhodamine.

6. The method of claim 1, wherein T has the formula $-CR_cR_d-NR_eR_f$ where
  $R_c$ and $R_d$ are independently selected from the group consisting of hydrogen and an alkyl having 1-16 carbons; and
  $R_e$ is alkyl and $R_f$ is an alkyl group having 1-16 carbon atoms or
  N, $R_e$ and $R_f$ form a nitrogen heterocyclic ring system selected from the group consisting of morpholine, piperidine, pyrrolidine, piperazine, imidazole, oxazepine, azepine, pyrrole and an alkyl substituted nitrogen heterocyclic system with the alkyl having 1-18 carbons.

7. The method of claim 6, wherein amine substituents $R_e$ and $R_f$ form a nitrogen heterocycle selected from the group consisting of pyrrolidine, piperidine, piperazine, morpholine, imidazole, azepine and oxazepine.

8. The method of claim 1, wherein T has the formula $-CR_cR_d-NR_eR_f$ where:
  a) $R_c$ and $R_d$ are independently selected from the group consisting of hydrogen and an alkyl having 1-16 carbons;
  b) $R_e$ and $R_f$ are alkyl groups.

9. The method of claim 8, where said alkyl groups $R_e$ and $R_f$ are substituted by a group selected from the group consisting of halogen, carboxamide, oxy, hydroxy, mercapto and cyano.

10. The method of claim 8, wherein amine substituents $R_e$ and $R_f$ are independently an alkyl group having 1-6 carbons.

11. The method of claim 1, wherein said substrate is present in a concentration greater than 10 uM and less than 500 uM.

12. The method of claim 1, further comprising adding an additional detection reagent to said sample.

13. The method of claim 12, wherein said additional detection reagent is selected from the group consisting of a membrane probe, a mitochondrial stain and a nucleic acid stain.

14. The method of claim 1, wherein said step of detecting a visible signal comprises illuminating said sample with an excitation source at a wavelength greater than 350 nm and detecting a fluorescence response in said sample.

15. The method of claim 14, wherein said sample comprises an abnormal cell mammalian.

16. The method of claim 15 wherein the presence of said visible signal is indicative of a disease state present in said cell abnormal mammalian.

17. The method of claim 14, wherein the step of detecting a fluorescence response is performed using a an instrument selected from the group consisting of a microscope, a fluorometer, a microtiter plate reader, and a flow cytometer.

18. The method of claim 14, further comprising sorting said mammalian cells based on the fluorescent response.

19. The method of claim 1, wherein the presence of said visible signal is indicative of a metabolic response to drug activity in said acidic organelle.

20. A method of detecting native sulfatase activity in acidic organelles comprising
   a) combining a sample that comprises mammalian cells with a solution comprising a substrate:

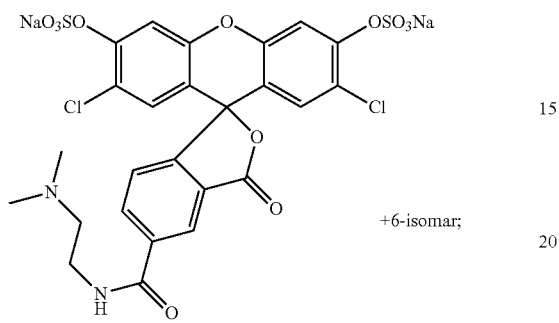

+6-isomar;

and
   (b) detecting the presence of a visible signal, wherein said sample is combined with said substrate in a concentration greater than 10 μM and less than 2 mM for a time sufficient for said native sulfatase to remove a sulfate group from said substrate to produce said visible signal.

* * * * *